United States Patent
Zhang et al.

(10) Patent No.: US 8,884,037 B2
(45) Date of Patent: Nov. 11, 2014

(54) METHOD OF REDUCING THE VALUE OF AN ALKYLENE OXIDE PRODUCTION PARAMETER IN A PROCESS OF MAKING AN ALKYLENE OXIDE USING A HIGH EFFICIENCY CATALYST

(75) Inventors: Liping Zhang, Lake Jackson, TX (US); Ravindra Tupe, Helsinki (FI)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 13/989,321

(22) PCT Filed: Dec. 9, 2011

(86) PCT No.: PCT/US2011/064077
§ 371 (c)(1),
(2), (4) Date: May 23, 2013

(87) PCT Pub. No.: WO2012/078948
PCT Pub. Date: Jun. 14, 2012

(65) Prior Publication Data
US 2013/0245296 A1    Sep. 19, 2013

Related U.S. Application Data

(60) Provisional application No. 61/421,968, filed on Dec. 10, 2010.

(51) Int. Cl.
*C07D 301/10*   (2006.01)
*C07D 301/22*   (2006.01)

(52) U.S. Cl.
CPC ............ *C07D 301/10* (2013.01); *C07D 301/22* (2013.01)
USPC .......................................................... 549/534

(58) Field of Classification Search
CPC ...... C07D 301/10; B01J 23/50; B01J 8/0285; B01J 8/067
USPC .................... 549/534; 422/198, 652; 502/347
See application file for complete search history.

(56) References Cited

U.S. PATENT DOCUMENTS

| | | |
|---|---|---|
| 5,187,140 A | 2/1993 | Thorsteinson et al. |
| 7,507,845 B1 | 3/2009 | Gueckel |
| 7,615,655 B2 | 11/2009 | Zhang et al. |
| 7,657,331 B2 | 2/2010 | Chipman et al. |
| 2004/0014999 A1 | 1/2004 | Chipman et al. |

(Continued)

FOREIGN PATENT DOCUMENTS

| | | |
|---|---|---|
| CN | 1437590 A | 8/2003 |
| EP | 0352850 B1 | 1/1994 |

(Continued)

OTHER PUBLICATIONS

International Search Report and Written Opinion dated, Apr. 2, 2012.

(Continued)

*Primary Examiner* — T. Victor Oh
(74) *Attorney, Agent, or Firm* — Hansen IP Law PLLC

(57) ABSTRACT

Methods of reducing the value of an alkylene oxide production parameter (such as alkylene oxide production rate) in a process of making an alkylene oxide by reacting an alkylene and oxygen over a high efficiency catalyst are shown and described. One method comprises reducing the concentration of oxygen in the reactor feed gas to reduce the value of the alkylene oxide production parameter.

15 Claims, 15 Drawing Sheets

(56) References Cited

U.S. PATENT DOCUMENTS

2010/0267972 A1 10/2010 Zhang et al.
2010/0267974 A1 10/2010 Zhang et al.
2010/0267975 A1 10/2010 Habenschuss et al.

FOREIGN PATENT DOCUMENTS

| | | |
|---|---|---|
| EP | 1458699 B1 | 11/2005 |
| WO | 0196324 A2 | 12/2001 |
| WO | 2008141030 A1 | 11/2008 |

OTHER PUBLICATIONS

International Preliminary Report On Patentability (IPRP) dated, Dec. 3, 2012.

Amendment and Response to Written Opinion, as-filed, dated Sep. 25, 2012.

Othmer, Kirk, "Ethylene Oxide", Encyclopedia of Chemical Technology, vol. 10, pp. 632-673 (Feb. 14, 2005).

English Translation of CN1437590A from Lexis Nexis Total Patent, by Chipman et al, Aug. 20, 2003.

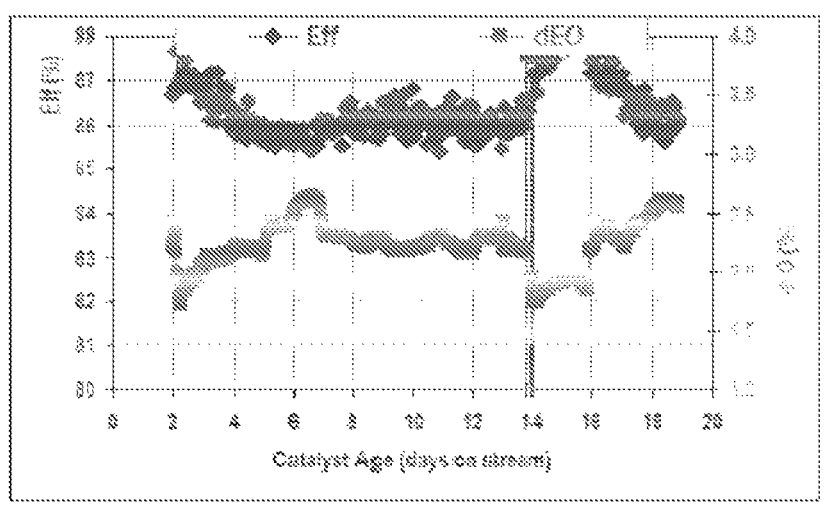

METHOD OF REDUCING THE VALUE OF AN ALKYLENE OXIDE PRODUCTION PARAMETER IN A PROCESS OF MAKING AN ALKYLENE OXIDE USING A HIGH EFFICIENCY CATALYST

TECHNICAL FIELD

This disclosure relates generally to processes for making alkylene oxides, and more specifically, to a method of reducing the value of an alkylene oxide production parameter (i.e., a variable that relates to the extent to which alkylene oxides are produced) in alkylene oxide production processes using high efficiency catalysts.

BACKGROUND

Alkylene oxides are known for a multiplicity of utilities. Ethylene oxide, for example, is used to produce ethylene glycol, which is used as an automotive coolant, as antifreeze, and in preparing polyester fibers and resins, nonionic surfactants, glycol ethers, ethanolamines, and polyethylene polyether polyols. Propylene oxide is used to produce propylene glycol and polypropylene polyether polyols, which are used in polyurethane polymer applications.

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

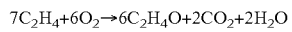

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than 0.1%/ppm) over a wide range of promoter concentrations, and this invariance is unaltered as reaction temperature is changed (i.e., the change in efficiency with respect to a change in reaction temperature is less than 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration can remain the same during the entire lifetime of a conventional catalyst. Alternatively, the reaction temperature may be adjusted to obtain a desired production rate without any substantial impact on efficiency.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least 0.2%/ppm when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age as well as other conditions such as feed gas composition. Moreover, the efficiency curves and the optimum gas phase promoter concentration tend to be strong functions of reaction temperature and are thus significantly affected if reaction temperature is varied, for example, to compensate for decreases in catalyst activity, (i.e., the change in efficiency with respect to a change in reaction temperature can be at least 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

Many commercial alkylene oxide processes are operated to achieve a targeted value of an alkylene oxide production parameter, such as the concentration of the alkylene oxide in the reaction product, alkylene oxide production rate, alkylene oxide production rate/catalyst volume, alkylene oxide yield, alkylene conversion, and oxygen conversion. In order to maximize conversion of the alkylene, many known processes maintain the maximum reactor feed gas oxygen concentration that is allowable based on feed gas flammability considerations. Neither the alkylene nor oxygen is stoichiometrically limiting, and some amount of each is contained in the reaction product. When a reduction in the alkylene oxide production parameter is desired, reaction temperature is frequently reduced. The reduction in reaction temperature reduces the overall rate of consumption of alkylene and oxygen. However, it can also cause a significant shift in the efficiency of the process, resulting in the excessive generation of unwanted byproducts such as carbon dioxide and water.

Because of the strong influence that reaction temperature may have on efficiency, the gas phase promoter concentration is often varied to counteract any efficiency decreases from the maximum attainable level that result from a reduction in reaction temperature. To coordinate the variations in reaction temperature and gas phase promoter concentration, it has been proposed to use the temperature differential to first calculate the new gas phase promoter concentration. The gas phase promoter concentration changes are made whenever the reaction temperature is changed (U.S. Pat. No. 7,193,094; European Patent No. 1,458,699). However, this technique may impose significant swings in the process variables and may require an excessive amount of time before the desired results are observed. It also requires knowledge of a mathematical relationship between temperature and efficiency, which may be difficult or costly to obtain. Thus, a need has arisen for a process of reducing the value of an alkylene oxide production parameter which addresses the foregoing issues.

SUMMARY

In accordance with a first aspect of the present disclosure, a method for reducing the value of an alkylene oxide production parameter in a process for making the alkylene oxide by reacting a feed gas comprising an alkylene, oxygen, and at least one organic chloride over a high-efficiency silver catalyst is provided. The method comprises operating the process at a first reaction temperature, a first overall chloriding effectiveness, and a first concentration of oxygen in the feed gas to yield a first value of the alkylene oxide production parameter. The method further comprises selecting a target value of the alkylene oxide production parameter which is less than the first value of the alkylene oxide production parameter. At least one process parameter is adjusted such that the alkylene oxide production parameter decreases, wherein the step of adjusting at least one alkylene oxide production parameter comprises first decreasing the concentration of oxygen in the feed gas.

In accordance with another aspect of the present disclosure, a process for reducing the value of an alkylene oxide production parameter is provided. The process comprises reacting a feed gas comprising an alkylene, oxygen, and at least one organic chloride over a high efficiency silver catalyst to yield a reaction product having a first value of the alkylene oxide production parameter, wherein the feed gas has a first overall catalyst chloriding effectiveness value and a first oxygen concentration, and the reaction is carried out at a first reaction temperature and a first feed gas pressure. The method further comprises selecting a target value of the alkylene oxide production parameter and decreasing the concentration of oxygen in the feed gas to a second oxygen concentration while maintaining the overall chloriding effectiveness value at the first overall chloriding effectiveness value until the alkylene oxide production parameter is no greater than the target value or the reaction temperature decreases by a preselected maximum amount.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 10C is a graph depicting efficiency and reactor product delta ethylene oxide concentration data used to illustrate the exemplary method of FIG. 10A;

DETAILED DESCRIPTION

Figure 1A:
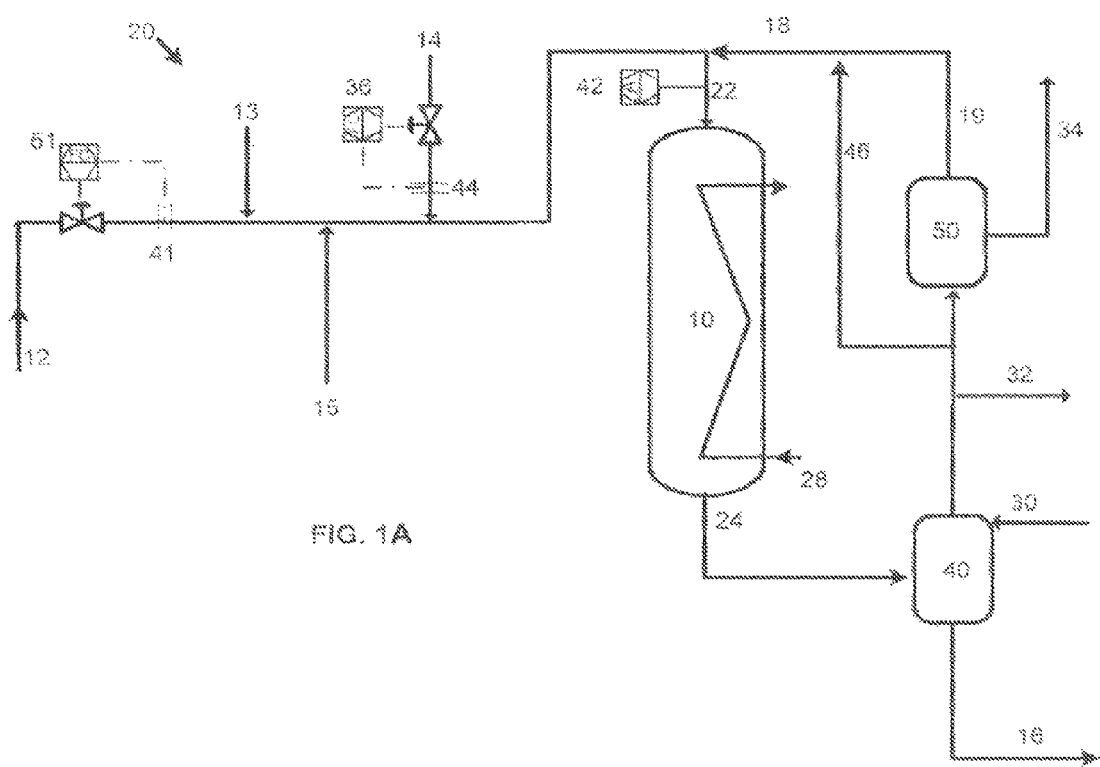
FIG. 1A is a process flow diagram depicting an embodiment of a process for making an alkylene oxide by epoxidizing an olefin over a high efficiency catalyst.

As discussed below, the present disclosure provides a method for reducing the value of an alkylene oxide production parameter while maintaining a maximum efficiency toward the alkylene oxide by reducing at least one process parameter comprising feed gas oxygen concentration in a process of manufacturing an alkylene oxide by reacting an alkylene, oxygen, and at least one organic chloride over a high-efficiency catalyst. In certain embodiments, decreasing oxygen alone will be insufficient to obtain the desired value of the alkylene oxide production parameter. In such cases, the concentration of alkylene in the reactor feed gas and/or the reactor pressure may also be reduced, and/or the concentration of carbon dioxide in the feed gas may be increased, either concurrently with or subsequent to the reduction in oxygen concentration. In certain preferred embodiments, the disclosed techniques allow the alkylene oxide production parameter to be reduced while maintaining the process at or close to an optimum operating condition. In other preferred embodiments, the methods are carried out after establishing an initial operating condition at which the reactor feed gas oxygen concentration is maintained at a maximum pre-selected value, such as may be dictated by a measure of flammability of the reactor feed gas.

In order to facilitate an understanding of the present disclosure, it is useful to define certain terms relating to catalyst and process performance. The activity of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, which are inactive towards the epoxidation reaction.

The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reaction temperature is maintained at a constant value; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. The "yield" of alkylene oxide refers to the net number of moles of alkylene oxide produced by the process divided by the net number of moles of olefin fed to the process for any given time period.

The term "alkylene oxide production parameter" is used herein to describe a variable that relates to the extent to which alkylene oxides are produced. Examples of alkylene oxide production parameters include, without limitation, alkylene oxide concentration, alkylene oxide yield, alkylene oxide production rate, alkylene oxide production rate/catalyst volume (also known as the alkylene oxide "work rate"), alkylene conversion, and oxygen conversion. The alkylene oxide concentration relates to the alkylene oxide production rate because the production rate may be obtained by multiplying the alkylene oxide concentration and the net product flow rate. Depending on the configuration of the process, an alkylene oxide production rate may be determined at the reactor outlet, downstream of a reactor outlet recycle stream, or downstream of separation processes (e.g., scrubbers) used to extract the alkylene oxide product. As used herein, the term "reaction product" includes unreacted feed components as well as those that are generated as a result of a chemical reaction. In the example of ethylene oxide processes, the "reaction product" would include ethylene oxide, and if present, any by-products (such as carbon dioxide) or unreacted feed components (such has ethylene, oxygen, and/or chlorides). The alkylene oxide production rate/catalyst volume may be determined by dividing the production rate by the volume of the catalyst bed. The oxygen and alkylene conversions are related to the production of the alkylene oxide by the efficiency.

FIG. 1A illustrates a process 20 for making an alkylene oxide. Process 20 includes a reactor 10 comprising a tubular vessel with a catalyst bed disposed in it. Olefin (i.e., alkylene) feed stream 12 (which may also include saturated hydrocarbons, such as ethane, as an impurity) is combined with ballast gas 13, oxygen feed 15 and gas phase promoter feed 14 to define reactor feed gas inlet stream 22 proximate the reactor inlet. Reactor product stream 24 includes the alkylene oxide ("AO") product, plus side products (e.g., $CO_2$, $H_2O$, and small amounts of saturated hydrocarbons), unreacted olefin, oxygen, and inerts. Water stream 30 is added to alkylene oxide absorber 40 to absorb alkylene oxide product from reactor product stream 24. Net product stream 16 comprises water and alkylene oxide, and the alkylene oxide is subsequently separated from the water.

If desired, recycle stream 18 may also be provided to reduce the amount of unreacted olefin in the net product stream 16. One example of a suitable recycle system is depicted in FIG. 1A. As shown in the figure, alkylene oxide absorber 40 produces an overhead gas stream comprising unreacted olefin, saturated hydrocarbon impurities or byproducts, and carbon dioxide. Carbon dioxide is removed in $CO_2$ removal unit 50 (e.g., a $CO_2$ scrubber) and exits $CO_2$ removal unit 50 in carbon dioxide stream 34. The overhead stream 19 from unit 50 is combined with $CO_2$ removal unit 50 bypass stream 46 to define recycle stream 18. Recycle stream 18 is combined with olefin feed 12, ballast gas 13, oxygen feed 15, and gas phase promoter feed 14 to define reactor feed stream 22. Purge line 32 is also provided to provide for the removal of saturated hydrocarbon impurities (e.g., ethane), inerts (such as argon), and/or byproducts (as well as carbon dioxide) to prevent their accumulation in reactor feed 22.

The olefin comprising olefin feed stream 12 may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1=CH_3$, $R_2=H$) and ethylene ($R_1=R_2=H$) are more preferred, and ethylene is most preferred. Correspondingly, preferred alkylene oxides in reactor product stream 24 are of the formula:

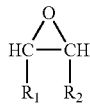

wherein, $R_1$ and $R_2$ are individually selected from the group consisting of hydrogen and alkyl radicals having from 1 to 6 carbon atoms. Propylene oxide ($R_1=CH_3$, $R_2=H$) and ethylene oxide ($R_1=R_2=H$) are more preferred, and ethylene oxide is most preferred.

Oxygen feed 15 may comprise pure oxygen or air. If pure oxygen is used, ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least one (1) mole percent, preferably at least two (2) mole percent, and still more preferably at least four (4) mole percent. The oxygen concentration will generally be no more than fifteen (15) mole percent, preferably no more than twelve (12) mole percent, and even more preferably no more than nine (9) mole percent. The ballast gas 13 (e.g., nitrogen or methane) is generally from 50 mole percent to 80 mole percent of the total composition of reactor feed stream 22. Methane ballast gas is preferred over nitrogen because, due to its higher heat capacity, it facilitates the use of higher oxygen concentrations in the cycle, and therefore, improves both activity and efficiency.

In certain exemplary processes, the concentration of oxygen in reactor feed 22 is set at a pre-selected maximum value which is no greater than an amount of oxygen that would form a flammable mixture with the components of reactor feed 22 at the prevailing process conditions (the "oxygen flammability concentration"). In other embodiments, the maximum oxygen concentration is no greater than a pre-defined percentage of the oxygen flammability concentration (e.g., the maximum oxygen concentration is no greater than 95% of the oxygen flammability concentration and preferably no greater than 90% of the oxygen flammability concentration). In certain further embodiments, the maximum oxygen concentration and/or the oxygen flammability concentration is determined based on at least one variable selected from the group consisting of reaction temperature, pressure, alkylene concentration, alkylene oxide concentration, ballast gas concentration, and carbon dioxide concentration in reactor feed 22.

The concentration of olefin in reactor feed stream 22 may vary over a wide range. However, it is preferably at least eighteen (18) mole percent and more preferably at least twenty (20) mole percent. The concentration of olefin in reactor feed stream 22 is preferably no greater than 50 mole percent, and more preferably is no greater than 40 mole percent.

The carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than 5 mole percent, preferably no more than 3 mole percent, and even more preferably no more than 2 mole percent of the total composition of reactor feed 22. Water is also a reaction by-product, and may be present in the feed gases in concentrations that are preferably from 0 to no more than three (3) mole percent.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communi-* cations, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to 2 mole percent. Given the competing effects of the gas phase promoter and the non-halogenated, non-promoting hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity $Z^*$ and represented by the following formula:

$$Z^* = \frac{\text{ethyl chloride equivalent } (ppmv)}{\text{ethane equivalent (mole percent)}} \quad (4)$$

wherein the ethyl chloride equivalent is the concentration in ppmv of ethyl chloride that provides the same catalyst chloriding effectiveness of the organic chlorides present in reactor feed stream 22 at the concentrations of the organic chlorides in feed stream 22; and the ethane equivalent is the concentration of ethane in mole percent that provides the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of $Z^*$ would then be 3 ppmv. As a further example, it has been found that for certain catalysts methyl chloride has 10 times less the chloriding effectiveness of ethyl chloride. Therefore, for such catalysts the ethyl chloride equivalent for a given concentration of methyl chloride in ppmv is 0.1×(methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0×(vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (1)) is the concentration of ethane in mole percent in reactor feed stream 22 plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed 22 having 30.0 mole percent ethylene and 0.3 mole percent ethane, the ethane equivalent will then be 0.6 mole percent. As another illustration, it has been found that for certain catalysts methane has 500 times less the dechloriding effectiveness of ethane. Thus, for such catalysts the ethane equivalent for methane is 0.002× (methane concentration in mol percent). For a hypothetical inlet reactor feed 22 having 30.0 mole percent ethylene and 0.1 mole percent ethane, the ethane equivalent then will be 0.4 mole percent. For an inlet reactor feed 22 having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the $Z^*$ calculation may be negligible.

Thus, given the foregoing relationships, in the case where reactor feed stream 22 includes ethylene, ethyl chloride, ethylene dichloride, vinyl chloride, and ethane, the overall catalyst chloriding effectiveness value of process 20 can be defined as follows:

$$Z^* = \frac{(ECL + 2*EDC + VCL)}{(C_2H_6 + 0.01*C_2H_4)} \quad (5)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter and the hydrocarbon dechlorinating species also be measured under the reaction conditions which are being used in the process. Z* will preferably be maintained at a level that is no greater than 20 and which is most preferably no greater than 15. Z* is preferably at least 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, and ethylene dichloride must be considered in calculating Z*.

The order in which the inlet gases (alkylene oxide and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1A, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature. The epoxidation reaction is carried out at a temperature that is preferably at least 200° C., more preferably at least 210° C., and most preferably at least 220° C. Reaction temperatures of no more than 300° C. are preferred, and reaction temperatures of no more than 290° C. are more preferred. Reaction temperatures of no more than 280° C. are most preferred. The reactor pressure is selected based on the desired mass velocity and productivity and ranges generally from 5 atm (506 kPa) to 30 atm (3.0 MPa). The gas hourly space velocity (GHSV) is preferably greater than 3000 $h^{-1}$, more preferably greater than 4,000 $hr^{-1}$, and most preferably greater than 5,000 $hr^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379, 134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least 80 weight percent α-alumina and less than 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least 0.5 $m^2/g$, and more preferably, at least 0.7 $m^2/g$. The surface area is typically less than 10 $m^2/g$, and preferably, less than 5 $m^2/g$. The alpha-alumina carrier preferably has a pore volume of at least 0.3 $cm^3/g$, and more preferably, from 0.4 $cm^3/g$ to 1.0 $cm^3/g$ and a median pore diameter from 1 to 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one flat major surface, and having a lamellate or platelet morphology. In a more preferred embodiment the particles approximate the shape of a hexagonal plate (some particles having two or more flat surfaces), at least 50 percent of which (by number) have a major dimension of less than 50 microns. In a preferred embodiment, the alpha-alumina carrier comprises zirconium silicate (zircon), present as zirconium silicate in the finished carrier, more preferably, in an amount up to 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140, incorporated herein by reference.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Typically, the amount of silver supported on the carrier is less than 70 percent, and more preferably, less than 50 percent by weight, based on the weight of the catalyst.

Although silver particle size in the finished catalyst is important, the range is not narrow. A suitable silver particle size can be in the range of from 10 to 10,000 angstroms in diameter. A preferred silver particle size ranges from greater than 100 to less than 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from 0.0005 to 1.0 wt. %, preferably from 0.005 to 0.5 wt. %. The preferred amount of cation promoter deposited on or present on the surface of the carrier or catalyst generally lies between 10 and 4000, preferably 15 and 3000, and more preferably between 20 and 2500 ppm by weight of cation calculated on the total carrier material. Cation promoter amounts between 50 and 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from 0.0001:1 to 10,000:1, preferably from 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $[SO_4]^{-2}$, phosphates, for example, $[PO_4]^{-3}$, titanates, e.g., $[TiO_3]^{-2}$, tantalates, for example, $[Ta_2O_6]^{-2}$, molybdates, for example, $[MoO_4]^{-2}$, vanadates, for example, $[V_2O_4]^{-2}$, chromates, for example, $[CrO_4]^{-2}$, zirconates, for example, $[ZrO_3]^{-2}$, polyphosphates, manganates, nitrates, chlorates, bromates, borates, silicates, carbonates, tungstates, thiosulfates, cerates, rheanates, perrhenates, and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $[MoO_4]^{-2}$, and $[Mo_2O_{24}]^{-6}$ and $[Mo_2O_7]^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylene-diamine-tetraacetic acid (EDTA) or a suitable salt thereof.

The amount of anion promoter may vary widely, for example, from 0.0005 to 2 wt. %, preferably from 0.001 to 0.5 wt. % based on the total weight of the catalyst. When used, the rhenium component is often provided in an amount of at least 1, say, at least 5, for example, 10 to 2000, often between 20 and 1000, ppmw calculated as the weight of rhenium based on the total weight of the catalyst.

It is desirable that the silver and one or more solid promoters be relatively uniformly dispersed on the carrier. A preferred procedure for depositing silver catalytic material and one or more promoters comprises: (1) impregnating a carrier according to the present invention with a solution comprising a solvent or solubilizing agent, silver complex and one or more promoters, and (2) thereafter treating the impregnated carrier to convert the silver compound and effect deposition of silver and the promoter (s) onto the exterior and interior pore surfaces of the carrier. Silver and promoter depositions are generally accomplished by heating the solution containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

Figure 1B:
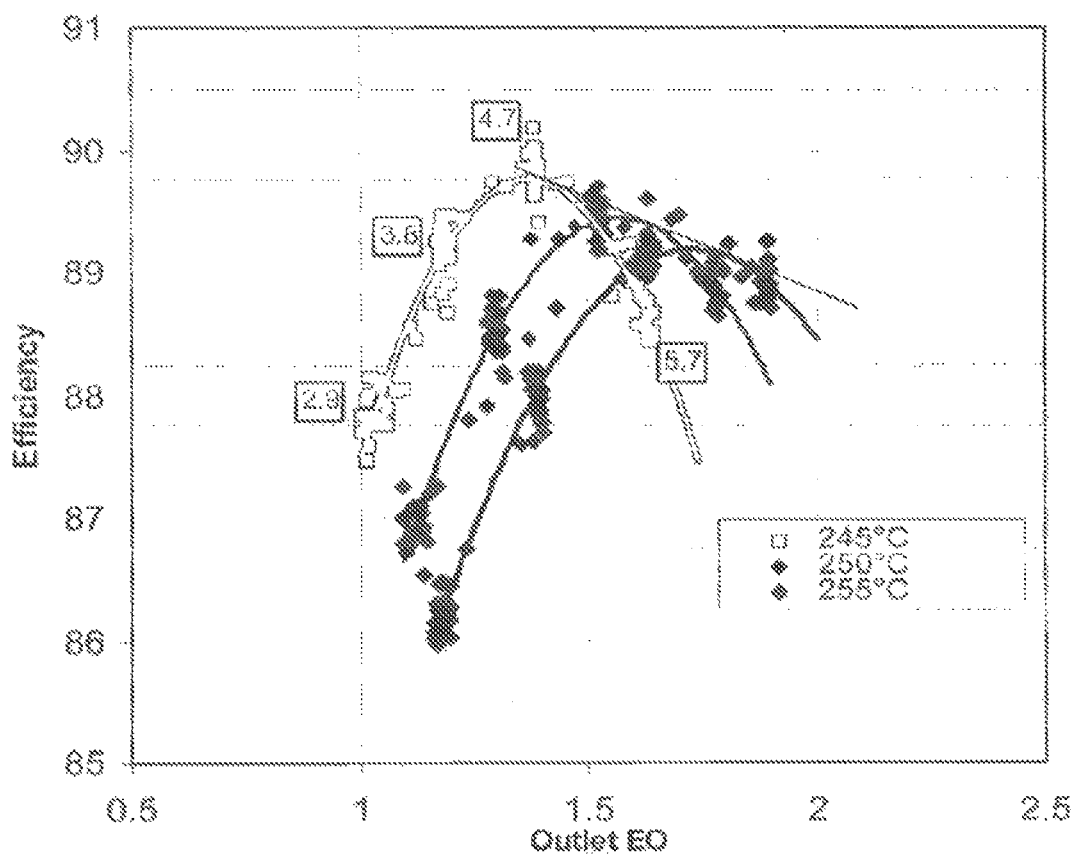
FIG. 1B is a series of curves depicting relationships between catalyst efficiency (selectivity) and reactor outlet ethylene oxide concentration at three different temperatures and four different overall catalyst chloriding effectiveness parameter values.

As is known in the art, the yield of alkylene oxide depends on the rate of olefin consumption, and the rates of competing side reactions. With conventional catalysts, a desired rate of alkylene oxide production can be achieved by varying reaction temperature without sacrificing efficiency substantially. However, with high efficiency catalysts, efficiency is typically dependent on both the overall catalyst chloriding effectiveness and the reaction temperature. Thus, a change that would increase the rate of olefin consumption may be accompanied by a corresponding decrease in efficiency. It is generally desirable to maximize efficiency to minimize the raw material consumption and the generation of unwanted byproducts (carbon dioxide and water). Because efficiency varies with both overall catalyst chloriding effectiveness and reaction temperature, both variables must typically be varied in order to obtain a desired alkylene oxide production parameter. FIG. 1B illustrates this phenomenon. The figure depicts reactor outlet ethylene oxide concentration and efficiency (selectivity) data for a high efficiency, rhenium-promoted silver catalyst operated at three different reaction temperatures (245° C., 250° C., and 255° C.) at four different values of the overall catalyst chloriding effectiveness parameter Z* (2.9, 3.8, 4.7, and 5.7, as shown in the squares in FIG. 1B) which were obtained by varying the inlet concentration of ethyl chloride. The same values of Z* were used for all three temperatures, but for simplicity only the graph for 245° C. is labeled with the Z* values. The temperatures increase moving from the top left of the graph to the bottom right of the graph, and each curve is generally parabolic. Thus, at a Z* value of 4.7, an outlet ethylene oxide concentration of about 1.4 mole percent is achieved at an efficiency of 89.8% when the reaction temperature is 245° C. However, for the same reactor outlet ethylene oxide concentration, the efficiency drops off to about 89.3% when the temperature is increased to 250° C., and drops further to about 88.3% when the temperature is increased to 255° C. As the figure also illustrates, if after operating at an ethylene oxide reactor outlet concentration of 1.4 mole percent at 245° C., it is desired to increase the amount of ethylene oxide to about 1.7 mole percent, simply increasing Z* to 5.7 without increasing the reaction temperature will produce the desired yield. However, the efficiency will drop off to about 88.5%. As a result, certain known methods such as those described in U.S. Pat. No. 7,193,094 emphasize the need to simultaneously change the overall catalyst chloriding effectiveness whenever reaction temperature is changed.

It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet coolant temperature or outlet temperature.

Given the foregoing relationships between reaction temperature, Z* and efficiency, using either variable to reduce the value of an alkylene oxide production parameter may be undesirable. If the reaction temperature is decreased significantly in a short time, the optimum chloriding level of the catalyst may not be maintained even if Z* is adjusted properly and promptly because it may take a high-efficiency catalyst several days to reach steady state following a change in Z. In certain cases, Z* is not manipulable with sufficient sensitivity to control an alkylene oxide production parameter due to limitations in the ability to tightly measure and control the flow rate of gas phase promoters. In addition, in some cases the use of Z* to control an alkylene oxide production parameter can lead to operation at Z* values which in some circumstances would cause irreversible catalyst damage.

It has been discovered that variables other than reaction temperature and overall chloriding effectiveness may be changed in a manner that reduces the rate of alkylene and oxygen consumption without causing the process to deviate significantly from an optimum efficiency. As a result, an alkylene oxide production parameter may be reduced from an initial value without sacrificing efficiency. The variables that may be used to reduce the value of an alkylene oxide production parameter in accordance with the methods described herein include feed gas oxygen concentration (or partial pressure), feed gas alkylene concentration (or partial pressure), reactor feed gas inlet pressure, and carbon dioxide concentration (or partial pressure).

Figure 2:
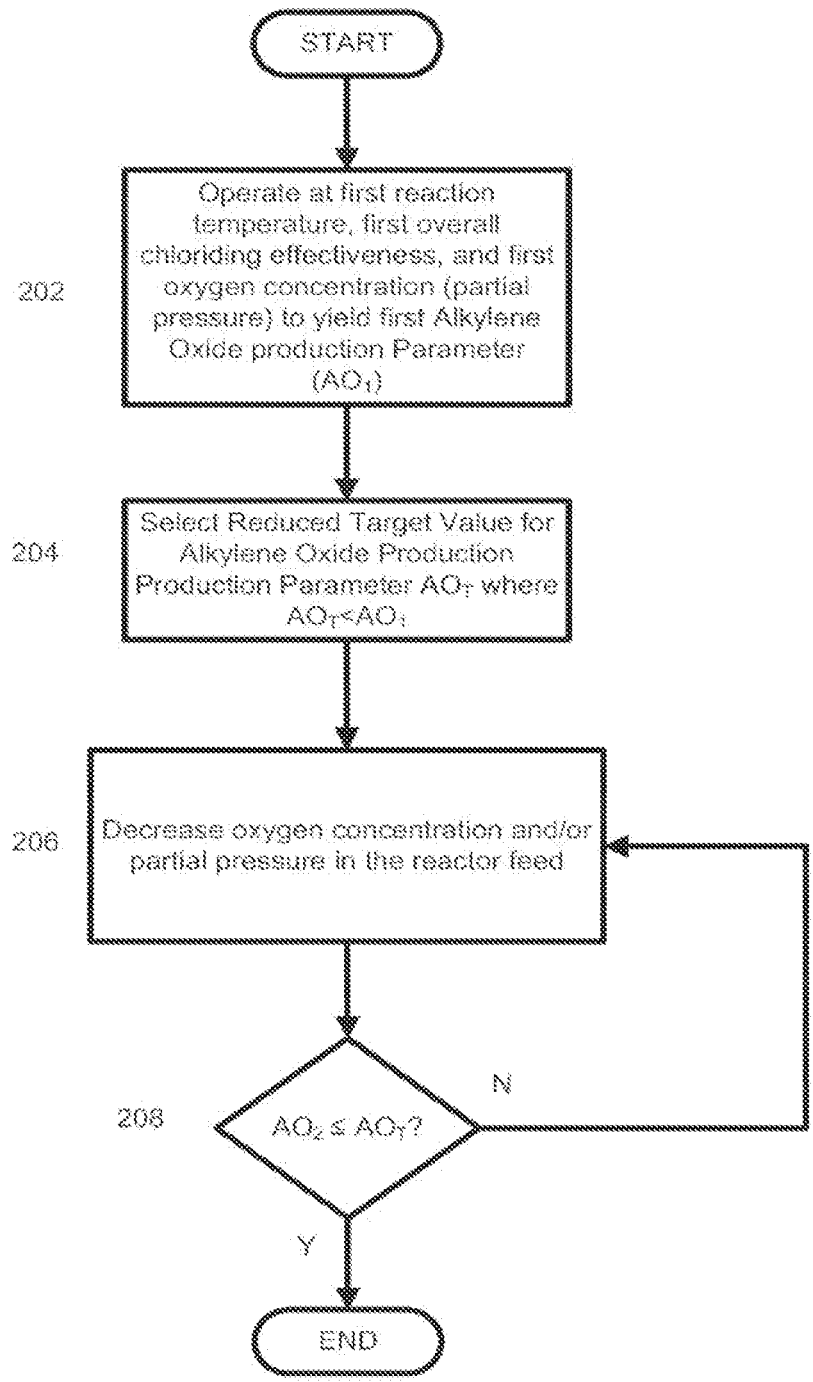
FIG. 2 is a flow chart depicting a first embodiment of a method for reducing the value of an alkylene oxide production parameter in the process of FIG. 1A.

Referring to FIG. 2, a method of reducing the value of an alkylene oxide production parameter will now be described. In accordance with the method, in step 202 process 20 is operated at an initial operating condition comprising a first reaction temperature, a first overall chloriding effectiveness, a first oxygen concentration, a first alkylene concentration, and a first reaction pressure to yield a first value of the alkylene oxide production parameter ($AO_1$). As is known to those skilled in the art, the partial pressures of gas components may be calculated by multiplying the molar fractions of the components by the total absolute pressure. Thus, the first concentration of oxygen and the first reactor feed gas inlet pressure will define and correspond to a first oxygen partial pressure. Similarly, the first concentration of the alkylene and the first reactor feed gas inlet pressure will define and correspond to a first alkylene partial pressure. A variety of methods may be used to select the initial operating condition used in step 202, several of which will be described below. In certain preferred embodiments, the initial operating condition will comprise an optimum operating condition. In other preferred embodiments, the concentration of oxygen in the feed gas at the initial operating condition will be a pre-selected maximum concentration. In certain examples, the pre-selected maximum oxygen concentration will be based on the oxygen flammability concentration. Pre-selected maximum molar oxygen concentrations (in mole percent) of no greater than 0.95 and 0.90 of the oxygen flammability concentration are preferred and more preferred, respectively. In step 204, a reduced target value ($AO_T$) for the alkylene oxide production parameter is selected. In one example, a downstream unit such as an alkylene glycol unit may develop a bottleneck which reduces the amount of alkylene oxide it can receive. In such a case, it may be desirable to reduce the rate of alkylene oxide production from process 20. In other examples, market conditions may dictate a reduction in the rate of production of the alkylene oxide.

It has been discovered that the concentration of oxygen in the reactor feed gas 22 can be decreased to achieve a reduced target alkylene oxide production parameter value without significantly deviating from an optimum operating condition. The change in the oxygen concentration will preferably yield a new value for the alkylene oxide production parameter $AO_2$, which is less than the first value of the parameter, $AO_1$. Thus, in step 206 the concentration of oxygen in the reactor inlet feed gas stream 22 is decreased by a selected amount. The reduction in the oxygen concentration may be carried out in a number of ways, including one or more step changes, one or more ramp changes, one or more non-linear changes, and various combinations of step, ramp, and non-linear changes. In one example, the flow rate of oxygen feed gas stream 15 is reduced (or the flow rate of an air stream is reduced in processes that use air for the epoxidation). The concentration of oxygen is preferably reduced while maintaining the overall chloriding effectiveness at the first overall chloriding effectiveness value established in step 202. During step 206, the partial pressure of oxygen is also preferably reduced, such as would be the case if the concentration of oxygen were reduced while the reactor pressure was held constant or decreased.

In certain exemplary embodiments, the reduction in feed gas oxygen concentration is carried out with the reaction temperature controller in open loop so that the temperature can be used to indicate the effect of the oxygen reduction on the optimum operation of process 20. In accordance with such examples, the reduction in feed gas oxygen concentration in step 206 yields a temperature decrease that is no greater than a pre-selected maximum amount. The pre-selected maximum decrease is preferably no greater than 5° C., more preferably no greater than 4° C., still more preferably no greater than 3° C., and even more preferably no greater than 2° C. In other examples, the oxygen concentration in reactor feed 22 is preferably reduced to no less than one (1) mole percent, more preferably to no less than two (2) mole percent, and still more preferably to no less than four (4) mole percent. In additional examples, the reduction in the oxygen concentration yields an oxygen partial pressure that is preferably no less than 7 kPa, more preferably no less than 14 kPa, and still more preferably no less than 30 kPa.

In step 208 the new parameter value $AO_2$ is compared to the target value $AO_T$. If the new parameter value is less than or equal to the target value, the process is terminated. If not, the concentration of oxygen is further reduced until the target value $AO_T$ is reached. However, the concentration of oxygen in the reactor feed gas 22 is preferably not reduced below the values above. If it becomes desirable to do so, the alkylene oxide production parameter can later be raised back to $AO_1$ by raising the concentration of oxygen in reactor feed gas 22, subject to any intervening process changes which may have altered the maximum desirable oxygen concentration.

In certain preferred examples, the reduction in the concentration of oxygen in step 206 yields an efficiency to the alkylene oxide that deviates from an optimum efficiency (at the reduced oxygen concentration) by no more than preferably 1.0 percent, more preferably 0.8 percent, and even more preferably 0.5 percent. The optimum efficiency may be determined in a variety of different ways. In certain examples, the optimum efficiency is based on the combination of the alkylene oxide production parameter, reaction temperature, and overall chloriding effectiveness. In one exemplary scenario, the optimum efficiency is the maximum efficiency attainable based on the minimum attainable reaction temperature and the corresponding overall chloriding effectiveness that provides the maximum efficiency at the minimum attainable reaction temperature. The minimum attainable temperature will be dictated by the heat transfer constraints imposed by the reactor coolant system. In other examples, the optimum efficiency is the maximum efficiency obtainable at the resulting alkylene oxide production parameter $AO_2$ by varying the overall chloriding effectiveness (e.g., $Z^*$) at a constant concentration of the alkylene in the feed gas and a fixed process condition. In still other examples, at the fixed process condition, at least one of reactor feed gas inlet pressure, feed gas oxygen concentration, feed gas carbon dioxide concentration, and gas hourly space velocity is held constant. In further examples, each of these variables is held constant in determining the optimum efficiency as the overall chloriding effectiveness is varied.

Additional details of optimization methods will be described further below. Also, set forth below are several methods of indirectly determining an optimum operating point which are used in certain examples to determine an optimum efficiency that limits the extent to which the feed gas oxygen concentration is changed in order to reduce the value of an alkylene oxide production parameter.

Figure 3:
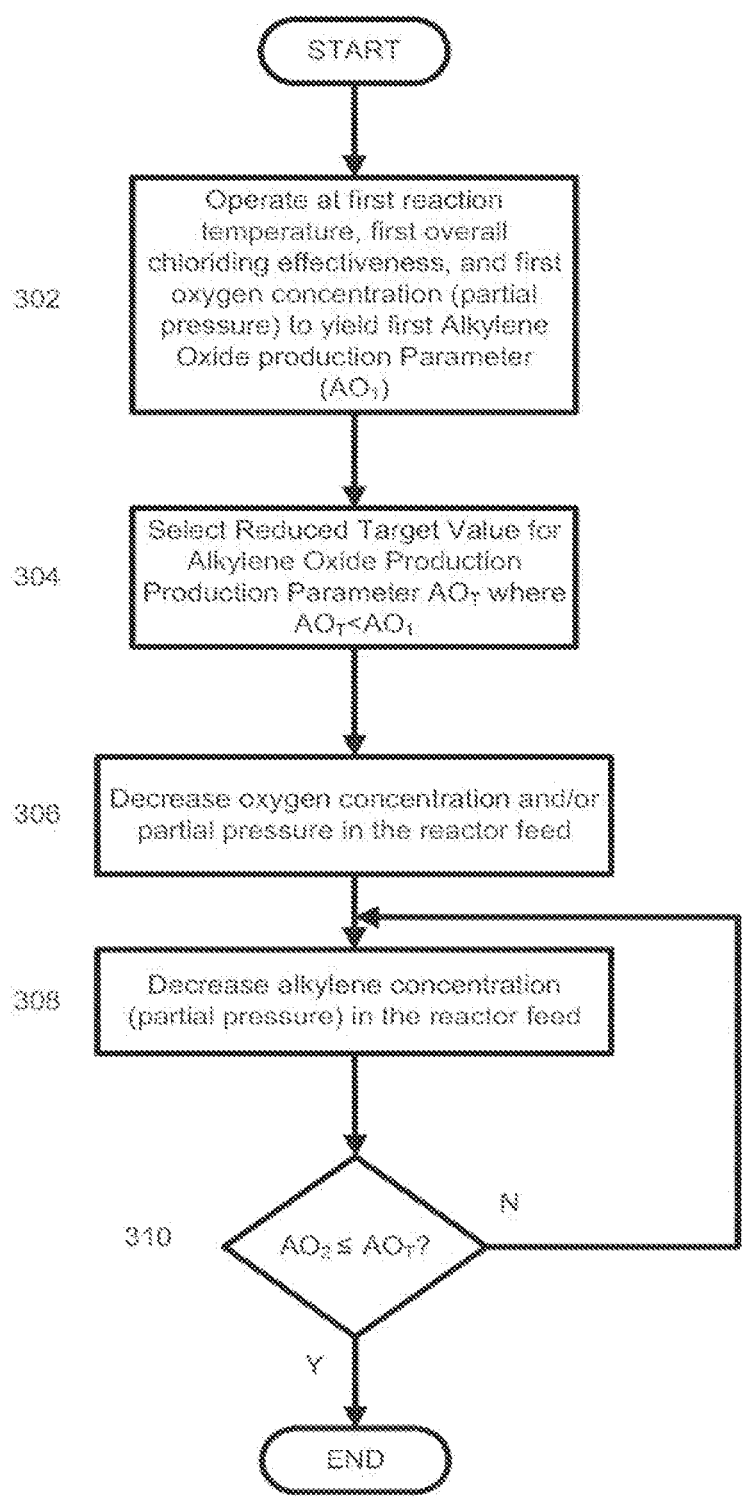
FIG. 3 is a flow chart depicting a second embodiment of a method for reducing the value of an alkylene oxide production parameter in the process of FIG. 1A.

Referring to FIG. 3, another exemplary method of reducing the value of an alkylene oxide production parameter is described. In accordance with the method, an initial operating condition is first selected at step 302 as in the case of step 202 of FIG. 2. The initial condition comprises a first reaction temperature, first overall chloriding effectiveness, first reaction pressure, first feed gas oxygen concentration (and corresponding partial pressure), and first feed gas alkylene concentration. The initial condition yields an initial value of the alkylene oxide production parameter $AO_1$.

In step 304, a target value $AO_T$ of the alkylene oxide production parameter is selected which is less than the initial target value $AO_1$. In step 306, the concentration of oxygen in the feed gas is reduced, which preferably causes the alkylene oxide production parameter to decrease. The decrease in the oxygen concentration is preferably accompanied by a reduction in the partial pressure of oxygen in the feed gas and is also preferably carried out while maintaining the overall chloriding effectiveness at the first overall chloriding effectiveness value. In certain preferred examples, the reduction in oxygen concentration is carried out in the manner and to the extent described for step 206 of FIG. 2.

In the embodiment of FIG. 3, the reduction in oxygen concentration is insufficient to reduce the alkylene oxide production value to the target value. Thus, in step 308, the concentration of alkylene in the feed gas is reduced, which preferably causes the alkylene oxide production parameter to decrease further. The reduction in the alkylene concentration is preferably accompanied by a reduction in the alkylene partial pressure. The reduction in alkylene concentration is preferably carried out while maintaining a constant value of the overall chloriding effectiveness. However, the alkylene concentration affects the overall chloriding effectiveness value. Thus, a compensating change is typically made to offset the change in the overall chloriding effectiveness which would otherwise result from decreasing the feed gas concentration of the alkylene. As indicated by the formula for $Z^*$ described above, a reduction in alkylene concentration will cause the overall chloriding effectiveness to increase. In one example, the concentration of the at least one organic chloride in the feed gas is reduced in a manner that offsets the effect of reducing the alkylene concentration.

In step 310, the resulting alkylene oxide production parameter value $AO_2$ is compared to the target value $AO_T$. If the new value $AO_2$ is less than or equal to the target value $AO_T$, the process is terminated. Otherwise, the concentration of alkylene is further reduced. If it becomes desirable to do so, the alkylene oxide production parameter can later be raised back to $AO_1$. In certain examples, this is preferably done by first increasing the alkylene concentration in the feed gas to its original value (and making the necessary adjustments to maintain a constant value of $Z^*$) and second (if necessary) increasing the oxygen concentration in the feed gas to its original value, subject to any intervening process changes which may have altered the maximum desirable oxygen concentration.

In certain preferred embodiments, during step 308 the concentration of alkylene in the reactor feed gas 22 is reduced to no lower than a pre-selected value. The pre-selected value is preferably at least 15 mole percent, more preferably at least 18 mole percent, and even more preferably at least 20 mole percent. The reduction in the alkylene concentration may be carried out in a number of ways, including one or more step changes, one or more ramp changes, one or more non-linear changes, and various combinations of step, ramp, and non-linear changes. In certain embodiments, the reduction in alkylene concentration is corresponds to a reduced partial pressure that is at preferably at least 97 kPa psia, more preferably at least 117 kPa, and even more preferably at least 131 kPa.

In certain preferred examples, the reduction in the concentration of the alkylene in step 308 yields an efficiency to the alkylene oxide that deviates from an optimum efficiency (at the reduced alkylene concentration) by no more than preferably 1.0 percent, more preferably, 0.8 percent, and even more preferably 0.5 percent. The optimum efficiency may be determined in a variety of different ways, including those described above with respect to FIG. 2 and additional methods discussed further below.

Figure 4:
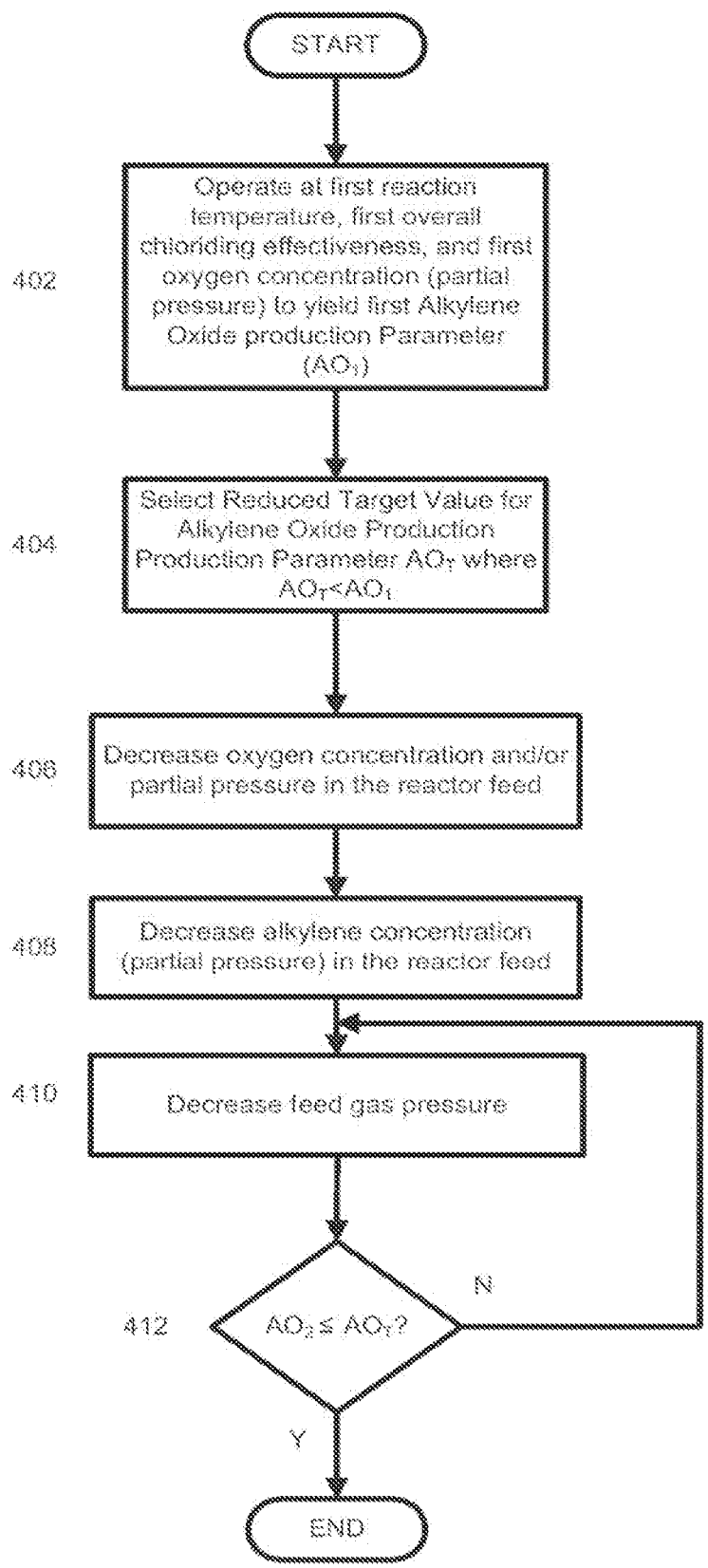
FIG. 4 is a flow chart depicting a third embodiment of a method for reducing the value of an alkylene oxide production parameter in the process of FIG. 1A.

Referring to FIG. 4, a further method of reducing the value of an alkylene oxide production parameter is described. In accordance with the method, an initial operating condition is selected in step 402, for example, in the same way that the initial operating conditions were selected in steps 202 and 302 in the methods of FIGS. 2 and 3. In step 404, a target value $AO_T$ of the alkylene oxide production parameter is selected which is less than the initial target value $AO_1$. In step 406, the concentration of oxygen is decreased in the manner described previously with respect to steps 206 and 306, preferably causing the alkylene oxide production parameter to decrease. In step 408, the concentration of the alkylene is decreased in the manner described previously with respect to step 308 of FIG. 3, which again preferably causes the alkylene oxide production parameter to decrease.

In the embodiment of FIG. 4, the reduction in oxygen and alkylene concentrations is not sufficient to reduce the alkylene oxide production parameter to the target value $AO_T$. Accordingly, in step 410, the reactor inlet feed gas pressure is decreased. For example, in certain commercial plants, a recycle gas compressor is provided with a discharge pressure controller, and the set point of the pressure controller may be reduced. The pressure reduction may be carried out in a variety of ways, including one or more step changes, one or more ramp changes, one or more non-linear changes, and various combinations of step, ramp, and non-linear changes. In certain preferred examples, the reduction in feed gas pressure is carried out while maintaining the overall chloriding effectiveness at the first overall chloriding effectiveness value established in step 402. The reduction in pressure will decrease the respective partial pressures of oxygen and the alkylene in the feed. However, in certain preferred examples their respective molar concentrations are held constant during step 410.

In step 412, the resulting alkylene oxide production parameter value $AO_2$ is compared to the target value $AO_T$. If the resulting parameter value $AO_2$ is less than or equal to the target value $AO_T$, the process is terminated. Otherwise, the reactor inlet feed gas pressure is further reduced. If it becomes desirable to do so, the alkylene oxide production parameter can later be raised back to $AO_1$. In certain examples, this is preferably done by first increasing the feed gas pressure to its original value, second (if necessary) increasing the alkylene concentration in the feed gas to its original value (and making the necessary adjustments to maintain a constant value of $Z^*$) and third (if necessary) increasing the oxygen concentration in the feed gas to its original value, subject to any intervening process changes which may have altered the maximum desirable oxygen concentration.

In certain illustrative embodiments, during step 410 the reactor inlet feed gas pressure is preferably reduced to no less than a pre-selected minimum value. In certain examples, the pre-selected minimum value is no less than 650 kPa, more preferably no less than 720 kPa, and even more preferably no less than 790 kPa. In other examples, the reactor inlet feed gas pressure is reduced by no more than a pre-selected amount (i.e., a maximum ΔP) during step 412. The pre-selected maximum pressure decrease is preferably no greater than 550 kPa, more preferably no greater than 480 kPa, and even more preferably no greater than 415 kPa. The minimum pressure is typically dictated by the design and operability of the equipment in the cycle loop.

In certain preferred examples, the reduction in the reactor inlet 22 feed gas pressure in step 410 yields an efficiency to the alkylene oxide that deviates from an optimum efficiency by no more than 1.0 percent, more preferably 0.8 percent, and even more preferably 0.5 percent. The optimum efficiency may be determined in a variety of different ways, including those described above with respect to FIG. 2 and those described below.

Figure 5:
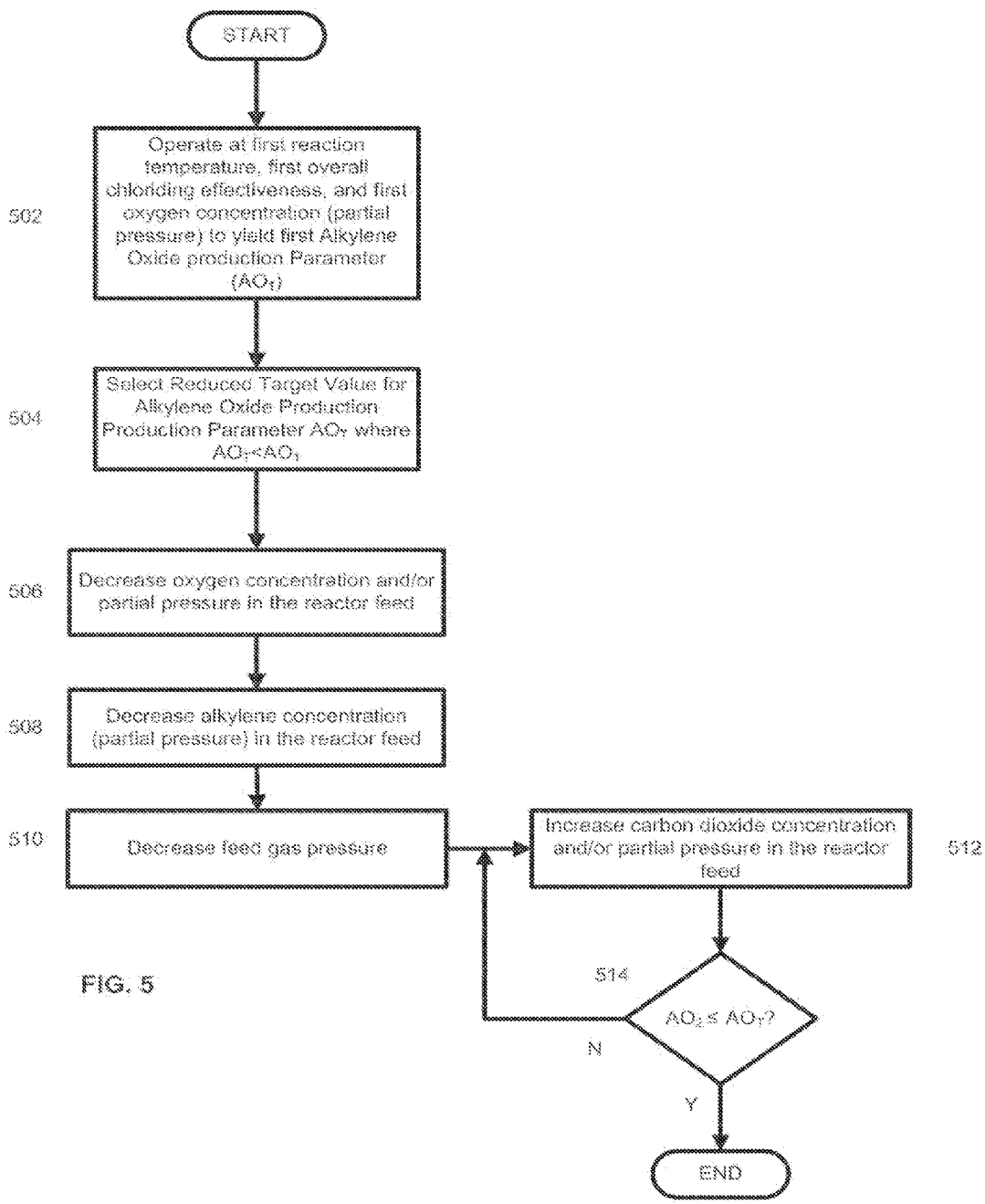
FIG. 5 is a flow chart depicting a fourth embodiment of a method for reducing the value of an alkylene oxide production parameter in the process of FIG. 1A.

Referring to FIG. 5, another method of reducing the value of an alkylene oxide production parameter is described. In accordance with the method, an initial operating condition is selected in step 502 in the same manner as steps 202, 302, and 402, described previously. In step 504, a target value $AO_T$ of the alkylene oxide production parameter is selected and is less than the initial value $AO_1$ corresponding to the initial operating condition of step 502.

In step 506 the concentration of oxygen in the reactor feed gas is reduced in the manner described previously with respect to steps 206, 306, and 406, preferably causing the alkylene oxide production parameter to decrease. In step 508 the concentration of the alkylene in the reactor feed gas is reduced in the manner described previously with respect to steps 308 and 408, preferably causing the alkylene oxide production parameter to further decrease. In step 510, the reactor inlet 22 feed gas pressure is reduced in the manner described previously with respect to step 410, preferably causing the alkylene oxide production parameter to further decrease.

In the method of FIG. 5, the reductions in oxygen concentration, alkylene concentration, and reactor inlet feed gas pressure are insufficient to reduce the alkylene oxide production parameter to the target value $AO_T$. Thus, in step 512, the concentration of carbon dioxide in the reactor inlet 22 feed gas is increased, preferably causing the alkylene oxide production parameter to decrease. The partial pressure of carbon dioxide in the reactor inlet 22 feed gas preferably increases as a result. In step 514, the alkylene oxide production parameter $AO_2$ is compared to the target value $AO_T$. If the resulting parameter value $AO_2$ is less than or equal to the target value $AO_T$, the process is terminated. Otherwise, the carbon dioxide pressure is further increased. If it becomes desirable to do so, the alkylene oxide production parameter can later be raised back to $AO_1$. In certain examples, this is preferably done by first decreasing the carbon dioxide concentration in the feed gas to its original value, second (if necessary) increasing the feed gas pressure to its original value, third (if necessary) increasing the alkylene concentration in the feed gas to its original value (and making the necessary adjustments to maintain a constant value of Z*) and fourth (if necessary) increasing the oxygen concentration in the feed gas to its original value, subject to any intervening process changes which may have altered the maximum desirable oxygen concentration.

Referring to FIG. 1A, the carbon dioxide concentration in the reactor feed gas inlet 22 can be reduced in a number of ways. In one method, the carbon dioxide removal unit bypass line 46 flow rate is decreased to route more of the total recycled gas through the removal unit 46. In another method, the process conditions used in carbon dioxide removal unit 46 are modified to remove more carbon dioxide from the recycle gas, thus increasing the flow rate of carbon dioxide stream 34. In examples wherein carbon dioxide removal unit 46 is a scrubber, the flow rate of the scrubbing medium (e.g., amine, NaOH) can be increased to increase carbon dioxide removal. In addition, the pressure of the scrubber can be increased and/or its temperature can be decreased to favor absorption of carbon dioxide in the scrubbing medium. In certain examples, the amount of carbon dioxide supplied via recycle stream 18 may be decreased to offset an increase in the carbon dioxide content of the fresh alkylene feed stream 12 or any other feed stream without increasing the concentration of carbon dioxide in reactor inlet feed stream 22 and thereby avoiding a decrease in the efficiency of the process to the alkylene oxide.

In certain preferred examples, the reduction in the reactor inlet 22 feed gas carbon dioxide concentration in step 512 yields an efficiency to the alkylene oxide that deviates from an optimum efficiency by no more than preferably 1.0 percent, more preferably 0.8 percent, and even more preferably 0.5 percent. The optimum efficiency may be determined in a variety of different ways, including those described above with respect to FIG. 2 and those described below.

As indicated by the foregoing discussion of FIGS. 2-5, in certain exemplary embodiments at least one process parameter selected from the group consisting of feed gas oxygen concentration, feed gas alkylene concentration, reactor inlet pressure, and feed gas carbon dioxide concentration and combinations thereof can be used to reduce the value of an alkylene oxide production parameter. Moreover, the process parameters may be varied sequentially or simultaneously. In addition, different combinations of the process parameters may be varied simultaneously and sequentially. For example, feed gas oxygen concentration and alkylene concentration may be reduced simultaneously followed by a reduction in feed gas pressure and/or feed gas carbon dioxide concentration.

Figure 6:
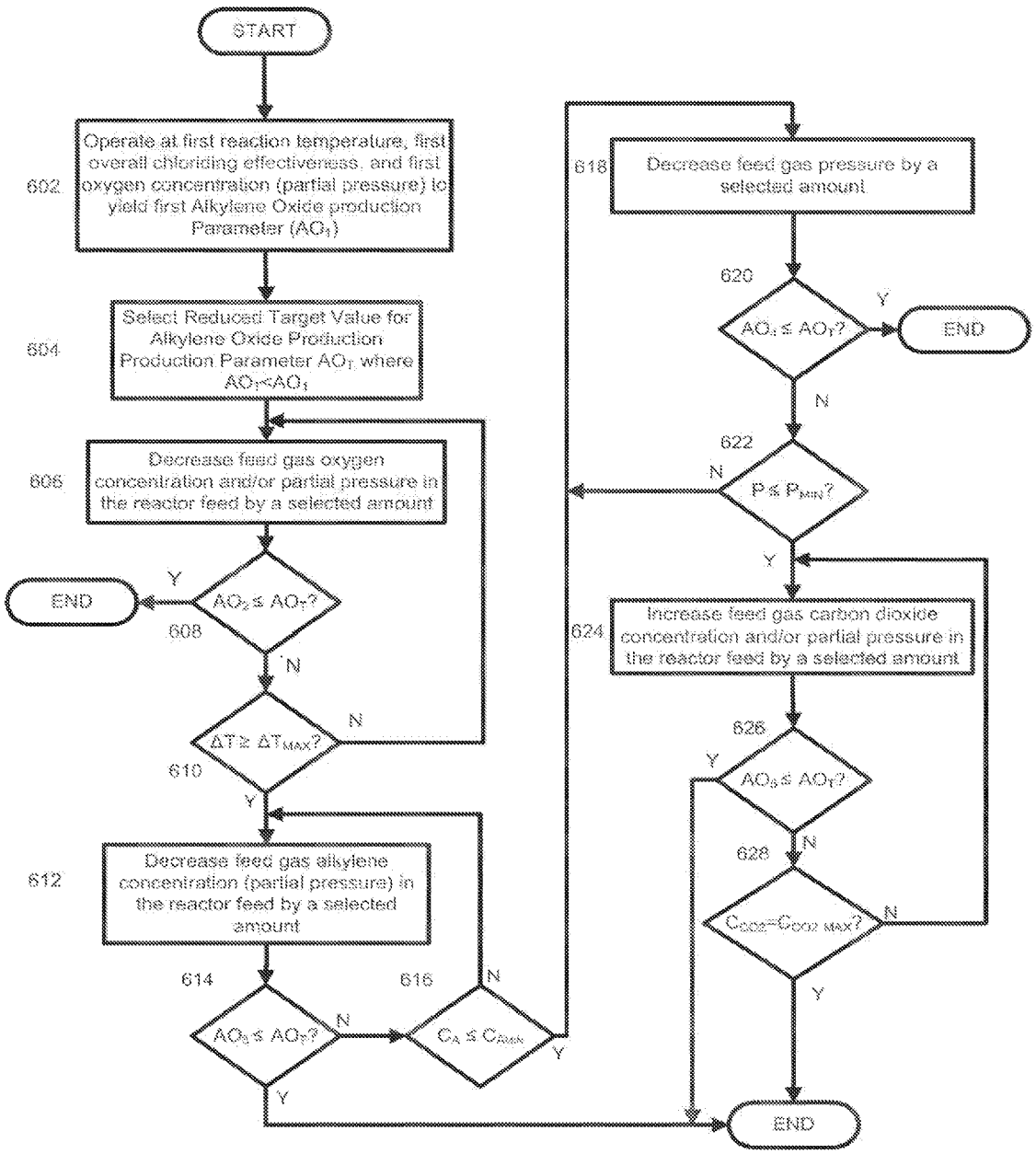
FIG. 6 is a flow chart depicting a fifth embodiment of a method for reducing the value of an alkylene oxide production parameter in the process of FIG. 1A.

One preferred exemplary technique for reducing the value of an alkylene oxide production parameter in accordance with the methods disclosed herein is depicted in FIG. 6. In accordance with the method, an initial operating condition is selected in step 602 in the manner described previously with respect to steps 202, 302, 402, and 502, yielding an initial alkylene oxide production parameter value $AO_1$. In step 604, a target value $AO_T$ of the alkylene oxide production parameter is selected, wherein the target value $AO_T$ is less than the initial value $AO_1$. In step 606, the concentration of oxygen in the reactor feed gas inlet 22 is decreased in the manner described previously for steps 206, 306, 406, and 506. The reduction in feed gas oxygen concentration preferably yields a reduction in the alkylene oxide production parameter from its initial value $AO_1$ to a new value $AO_2$. In addition, the reduction in feed gas oxygen concentration is preferably accompanied by a corresponding reduction in the partial pressure of oxygen in reactor feed gas inlet 22.

In step 608, the new value $AO_2$ of the alkylene oxide production parameter is compared to the target value $AO_T$. If the new value $AO_2$ is less than or equal to the target value $AO_T$, the process is terminated. However, if $AO_2$ is greater than $AO_T$, an efficiency-indicating parameter is used to determine whether any further decreases in oxygen concentration may cause an undesirable decline in the efficiency to the alkylene oxide. One such efficiency-indicating parameter is reaction temperature. In one method wherein step 606 is conducted without controlling the reaction temperature to a specified setpoint (i.e., with the temperature controller set on manual or in "open loop"), the reaction temperature change resulting from the decrease in feed gas oxygen concentration is monitored, and the reduction in oxygen concentration is manipulated to maintain a pre-selected maximum temperature decrease. An example of such a method is depicted in step 610 of FIG. 6. As indicated in the figure, the reaction temperature decrease $\Delta T$ is monitored and is compared to the pre-selected maximum temperature decrease $\Delta T_{max}$. If the reaction temperature decrease $\Delta T$ is less than the pre-selected maximum temperature decrease $\Delta T_{max}$, the method returns to step 604. However, if the reaction temperature decrease $\Delta T$ is greater than or equal to the pre-selected maximum temperature decrease $\Delta T_{max}$, the method proceeds to step 612. The value of $\Delta T_{max}$ is preferably 5° C., more preferably 4° C., still more preferably 3° C., and even more preferably 2° C. In certain preferred examples, step 606 is carried out while maintaining the overall chloriding effectiveness of the process at a constant value.

In certain preferred examples, the reduction in the concentration of oxygen in step 606 yields an efficiency to the alkylene oxide that deviates from an optimum efficiency by no more than 1.0 percent, more preferably 0.8 percent, and even more preferably 0.5 percent. The optimum efficiency may be determined in a variety of different ways, including those described above with respect to FIG. 2 and below.

In step 612, the concentration of alkylene in the reactor feed gas inlet 22 is decreased in the same manner as described above with respect to steps 308, 408, and 508. The reduction is preferably accompanied by a corresponding reduction in the partial pressure of the alkylene in the reactor feed gas inlet 22. As a result of the reduction in the feed gas alkylene concentration, the alkylene oxide production parameter preferably decreases from its previous value $AO_2$ to a new value $AO_3$. In step 614, the new alkylene oxide production parameter value $AO_3$ is compared to the target value $AO_T$. If $AO_3$ is less than or equal to $AO_T$, the method is terminated. Otherwise, the method proceeds to step 616 in which the concentration of the alkylene $C_A$ is compared to a pre-selected minimum alkylene concentration $C_{A\ MIN}$. If the alkylene concentration $C_A$ is less than or equal to the pre-selected minimum concentration $C_{AMIN}$, the method proceeds to step 618. Otherwise, the method returns to step 612, and the reactor feed gas alkylene concentration is further reduced. In certain preferred examples, step 612 is carried out while maintaining the overall chloriding effectiveness of the process at a constant value.

In certain preferred embodiments, during step 612 the concentration of alkylene in the reactor feed gas 22 is reduced to no lower than a pre-selected value. The pre-selected value is preferably at least 15 mole percent, more preferably, at least 18 mole percent, and even more preferably at least 20 mole percent.

In certain preferred examples, the reduction in the concentration of the alkylene in step 608 yields an efficiency to the alkylene oxide that deviates from an optimum efficiency by no more than preferably 1.0 percent, more preferably 0.8 percent, and even more preferably 0.5 percent. The optimum efficiency may be determined in a variety of different ways, including those described above with respect to FIG. 2 and below.

In step 618, the feed gas pressure is reduced by a selected amount, preferably resulting in a reduction in the alkylene oxide production parameter value from its previous value $AO_3$ to a new value $AO_4$. In step 620, the new value $AO_4$ is compared to the target value $AO_T$. If the new value $AO_4$ is less than or equal to the target value $AO_T$, the method is terminated. Otherwise, the method proceeds to step 622.

In step 622, the feed gas pressure P is compared to a pre-selected minimum feed gas pressure $P_{MIN}$. In certain examples, the pre-selected minimum value is no less than 650 kPa, more preferably no less than 720 kPa, and even more preferably no less than 790 kPa. In other examples, the reactor inlet feed gas pressure is reduced by no more than a pre-selected amount (i.e., a maximum $\Delta P$) during step 618. The pre-selected maximum pressure decrease is preferably no greater than 550 kPa, more preferably no greater than 480 kPa, and even more preferably no greater than 415 kPa. If the feed gas pressure P is less than or equal to the pre-selected minimum pressure $P_{MIN}$ (or if the pressure decrease $\Delta P$ exceeds the pre-selected maximum decrease $\Delta P_{MIN}$), the method proceeds to step 624. Otherwise, the method returns to step 618 and the pressure is further reduced.

In certain preferred examples, the reduction in the reactor inlet 22 feed gas pressure in step 618 yields an efficiency to the alkylene oxide that deviates from an optimum efficiency by no more than preferably 1.0 percent, more preferably 0.8 percent, and even more preferably 0.5 percent. The optimum or efficiency may be determined in a variety of different ways, including those described above with respect to FIG. 2 and below. In certain preferred examples, step 618 is carried out while maintaining the overall chloriding effectiveness of the process at a constant value.

In step 624, the concentration of carbon dioxide in the reactor feed gas inlet 22 is increased by a selected amount in the manner described previously with respect to step 512. The increase in carbon dioxide content preferably reduces the alkylene oxide production parameter from its previous value $AO_4$ to a new value $AO_5$. The increase in carbon dioxide concentration is preferably accompanied by a corresponding increase in the partial pressure of carbon dioxide in reactor feed as inlet 22. In certain examples, the concentration of carbon dioxide is increased while maintaining the overall chloriding effectiveness at a constant value.

In step 626, the new alkylene oxide production parameter $AO_5$ is compared to the target value $AO_T$. If the new value $AO_5$ is less than or equal to the target value $AO_T$, the method is terminated. Otherwise, the method proceeds to step 628. In step 628, the concentration of carbon dioxide in the reactor feed gas inlet 22 is determined. If the concentration is at its maximum, the method is terminated. Otherwise, the method returns to step 624 and the carbon dioxide concentration is further increased. If it becomes desirable to do so, the alkylene oxide production parameter can later be raised back to $AO_1$. In certain examples, this is preferably done by first decreasing the carbon dioxide concentration in the feed gas to its original value, second (if necessary) increasing the feed gas pressure to its original value, third (if necessary) increasing the alkylene concentration in the feed gas to its original value (and making the necessary adjustments to maintain a constant value of $Z^*$) and fourth (if necessary) increasing the oxygen concentration in the feed gas to its original value, subject to any intervening process changes which may have altered the maximum desirable oxygen concentration.

In certain preferred examples, the reduction in the reactor inlet 22 feed gas carbon dioxide concentration in step 624 yields an efficiency to the alkylene oxide that deviates from an optimum efficiency by no more than preferably 1.0 percent, more preferably 0.8 percent, and even more preferably 0.5 percent. The optimum efficiency may be determined in a variety of different ways, including those described above with respect to FIG. 2 and below.

As mentioned previously, both alkylene oxide concentration and alkylene oxide production rate may be used as an alkylene oxide production parameter in the methods described herein. If a target production (mass flow) rate $F_{AOT}$ is selected, the corresponding concentration $C_{AOT}$ may be calculated from the target mass flow rate, $F_{AOT}$ and the total reactor inlet volumetric flow rate (V) at standard temperature and pressure (273.15° K, 1 atm). In accordance with one method, the change in alkylene oxide concentration as a mole percentage ($\Delta AO$ %) is first calculated as follows:

$$\Delta AO\ \% = (F_{AOT}/MW_{AO})(RT/P)(100/V) \qquad (3)$$

wherein $MW_{AO}$ is the molecular weight of the alkylene oxide (e.g., 44.05 g/gmol for ethylene oxide). Based on $\Delta AO$ % and the reactor inlet concentration of the alkylene oxide ($C_{AO\ Inlet}$)/the following two equations are then simultaneously solved to obtain the outlet concentration of alkylene oxide in mole percent ($C_{AO1}$):

$$\text{Shrink Factor(SF)} = (200 + C_{AO\ Inlet})/(200 + C_{AOT}). \qquad (4)$$

$$\Delta AO\ \% = SF * C_{AOT} - C_{AO\ Inlet} \qquad (5)$$

The "Shrink Factor" represents the net volumetric reduction occurring due to the production of the alkylene oxide. For example, in the case of ethylene oxide production, for every mole of ethylene oxide produced, there is a net reduction of 0.5 moles of total gas resulting in a corresponding reduction in the volumetric flow rate.

The methods of FIGS. 2-6 all involve the selection of an initial operating condition and the manipulation of at least one process parameter to reduce the value of an alkylene oxide production parameter. As mentioned previously, in certain preferred examples, the manipulation of the at least one process parameter results in a deviation of the process from an optimum efficiency by no more than certain specified amounts. Several optimization methods may be used, including those described above with respect to FIG. 2. However, additional methods of defining an optimum condition for purposes of establishing the initial operating condition and/or for evaluating the impact of the process parameter manipulations may be used and will now be described. The methods are not themselves optimization techniques. However, it has been discovered that in certain embodiments, these methods can be used to identify an optimum operating condition and the corresponding efficiency to the alkylene oxide.

In one embodiment, an optimum operating condition is defined by selecting the process parameters to maintain the first derivative of efficiency with respect to reactor outlet alkylene oxide concentration at constant temperature, reactor inlet alkylene concentration, and a fixed process condition ($\partial E/\partial C_{AO}$) within a specified range. The fixed process condition is one in which at least one variable selected from the group consisting of pressure, reactor inlet oxygen concentration, reactor inlet carbon dioxide concentration, and gas hourly space velocity is held at a constant value. In one preferred embodiment, the fixed process condition is a condition at which each of pressure, reactor inlet oxygen concentration, reactor inlet carbon dioxide concentration and gas hourly space velocity is held constant.

In another embodiment, the preferred optimum operating condition is one that provides a reactor outlet alkylene oxide concentration ($C_{AO}$) that is higher than the efficiency-maximizing alkylene oxide concentration at an epoxidation temperature. In still another embodiment, the preferred optimum operating condition is selected to provide an overall chloriding effectiveness value that is higher than the efficiency-maximizing overall chloriding effectiveness value. In yet another embodiment, the optimum overall catalyst chloriding effectiveness value $Z_1^*$ and the initial reaction temperature $T_1$ are selected to maximize efficiency toward the alkylene oxide at the desired reactor outlet alkylene oxide concentration, $C_{AO1}$.

Other optimization methods and other methods of determining an optimum operating condition may also be used. For example, it may be desired to operate process 20 at the maximum catalyst efficiency for a given selected initial reaction temperature $T_1$ regardless of the alkylene oxide concentration in the reactor outlet 24. In addition, an efficiency maximizing scheme may be chosen by operating at the minimum obtainable reaction temperature (based on the capacity of coolant circuit 28) and by selecting the value of $Z_1^*$ that obtains the maximum efficiency. Alternatively, reactor outlet alkylene oxide concentration may be maximized regardless of the efficiency (as limited by the maximum temperature the reactor can withstand).

Methods of selecting or identifying a preferred optimum operating condition (e.g., T, $Z^*$, $C_{AO}$, E) will now be described. By way of illustration, the alkylene oxide production parameter used to illustrate the method is alkylene oxide concentration, $C_{AO}$. However, other alkylene oxide production parameters may be used. These methods may be used to select the initial operating condition of steps 202, 302, 402, 502, and 602. They may also be used to define the optimum operating state following the manipulation of a process parameter (e.g., feed gas oxygen concentration, feed gas alkylene concentration, reactor pressure, and feed gas carbon dioxide concentration). In addition, they may be used to constrain the extent to which any given process parameter is varied by providing feedback on the impact of the process parameter's variation on optimum process operation.

In accordance with a first exemplary embodiment, T and $Z^*$ are selected to correspond to a slope of efficiency versus reactor outlet alkylene oxide concentration that is within a selected range of values. The slope is the slope of efficiency versus reactor outlet alkylene oxide concentration as $Z^*$ is varied at constant temperature while holding reactor inlet alkylene concentration constant and operating at a fixed process condition. The fixed process condition is a condition at which at least one variable selected from the group consisting of reactor inlet oxygen concentration, reactor inlet carbon dioxide concentration, reactor pressure, and gas hourly space velocity is held constant. In a preferred embodiment, the fixed process condition is one at which each of these variables is held constant. The slope is preferably no greater than −1 percent efficiency/mole percent alkylene oxide, more preferably no greater than −1.5 percent efficiency/mole percent alkylene oxide, and even more preferably no greater than −2 percent efficiency/mole percent alkylene oxide. The slope is preferably at least −5 percent efficiency/mole percent alkylene oxide, more preferably at least −4.5 percent efficiency/mole percent alkylene oxide, and even more preferably at least −4 percent efficiency/mole percent alkylene oxide. A slope of −3 percent efficiency/mole percent alkylene oxide is especially preferred.

Figure 7A:
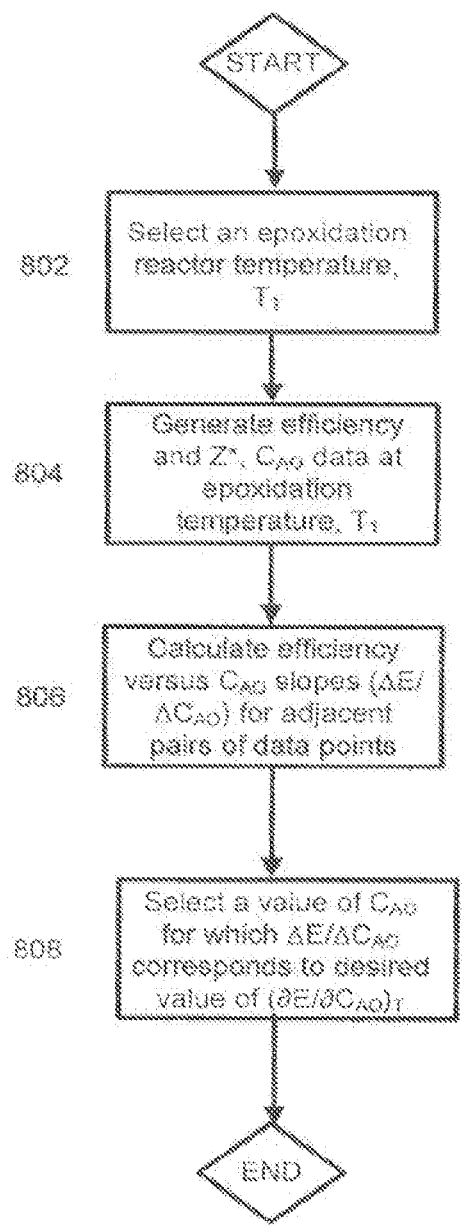
FIG. 7A is a flow chart depicting a first exemplary method of determining an optimum operating condition in the process of FIG. 1A.

Referring to FIG. 7A, a method of implementing the foregoing exemplary embodiment to select a preferred initial operating condition in steps 202, 302, 402, 502, and/or 602 is depicted. In accordance with the method, in step 802, a first selected reaction temperature, $T_1$ is selected to be an epoxidation reaction temperature that is at least 200° C., more preferably at least 210° C., and most preferably at least 220° C. $T_1$ is preferably no greater than 300° C., more preferably no greater than 290° C., and most preferably no greater than 280° C. In step 804, a first set of efficiency and $C_{AO}$ data is generated by varying $Z^*$ and measuring $C_{AO}$ and determining the efficiency at the various $Z^*$ values while holding the reaction temperature at the first selected reaction temperature $T_1$ and while holding reactor inlet alkylene concentration constant at a fixed process condition, as described above.

In step 806, the linear slopes defined by adjacent pairs of efficiency values and $C_{AO}$ values (e.g., $\Delta E/\Delta C_{AO}$) are determined at $T_1$. In step 808, a value of $C_{AO1}$ is selected at which $\Delta E/\Delta C_{AO}$ corresponds to a slope $(\partial E/\partial C_{AO})_T$ as described above. $Z_1^*$ and the optimum efficiency can then be determined from the collected data (e.g., by interpolation) based on the selected value of $\Delta E/\Delta C_{AO}$.

The method of FIG. 7A may be used to assess the impact of a particular process parameter on optimum operation, and as a result, may be used to limit the extent to which any particular parameter is reduced to achieve a target alkylene oxide production parameter value. For example, in step 306 of FIG. 3, the concentration of oxygen in the reactor feed gas stream 22 is reduced by a selected amount to reduce the value of the alkylene oxide production parameter AO. Following a particular reduction in the oxygen concentration, the process will operate at a new operating condition defined by a new oxygen concentration, a new reaction product alkylene oxide concentration, a new reaction temperature T, and preferably will operate at the same $Z^*$ value established in step 202. At the new operating condition, values of $\Delta E/\Delta C_{AO}$ may be determined, and the value of the slope $(\partial E/\partial C_{AO})_T$ may be determined at the new alkylene oxide concentration. If the slope is within a selected range, the oxygen concentration may be further reduced. Otherwise, it may be preferred to reduce a different process parameter such as by reducing the feed gas alkylene concentration in step 308 to achieve the desired target value $AO_T$ of the alkylene oxide production parameter. Thus, in certain examples, the reduction in feed gas oxygen concentration carried out in steps 206, 306, 406, 506, and 606 yields a new operating condition at which the slope $(\partial E/\partial C_{AO})_T$ is preferably less than zero percent efficiency/mole percent alkylene oxide, more preferably no greater than $-1.5$ percent efficiency/mole percent alkylene oxide, and even more preferably no greater than $-2$ percent efficiency/mole percent alkylene oxide. In other examples, the reduction in feed gas oxygen concentration carried out in steps 206, 306, 406, 506, and 606 yields a new operating condition at which the slope $(\partial E/\partial C_{AO})_T$ is preferably at least $-5$ percent efficiency/mole percent alkylene oxide, more preferably at least $-4.5$ percent efficiency/mole percent alkylene oxide, and even more preferably at least $-4$ percent efficiency/mole percent alkylene oxide. A slope of $-3$ percent efficiency/mole percent alkylene oxide is especially preferred.

In other examples, the reduction in alkylene concentration (steps 308, 408, 508, and 612), the reduction in reactor pressure (steps 410, 510, and 618), and/or the reduction in feed gas carbon dioxide concentration (steps 512 and 624) yield a slope $(\partial E/\partial C_{AO})_T$ falling within the ranges described above for reductions in feed gas oxygen concentration. Thus, the method of FIG. 7A allows the methods of FIGS. 2-6 to be carried out without deviating significantly from an optimum operating condition.

In accordance with another exemplary embodiment, the optimum operating condition used to set the initial operating condition and/or to define the impact of a process parameter change corresponds to an efficiency that is less than the maximum efficiency at the reaction temperature under which the process is operating. According to the method, the optimum operating condition is defined as one in which the alkylene oxide concentration is greater than the concentration corresponding to the maximum efficiency at the reaction temperature and/or in which the overall chloriding effectiveness is greater than the overall chloriding effectiveness corresponding to the maximum efficiency at the reaction temperature.

Figure 7B:
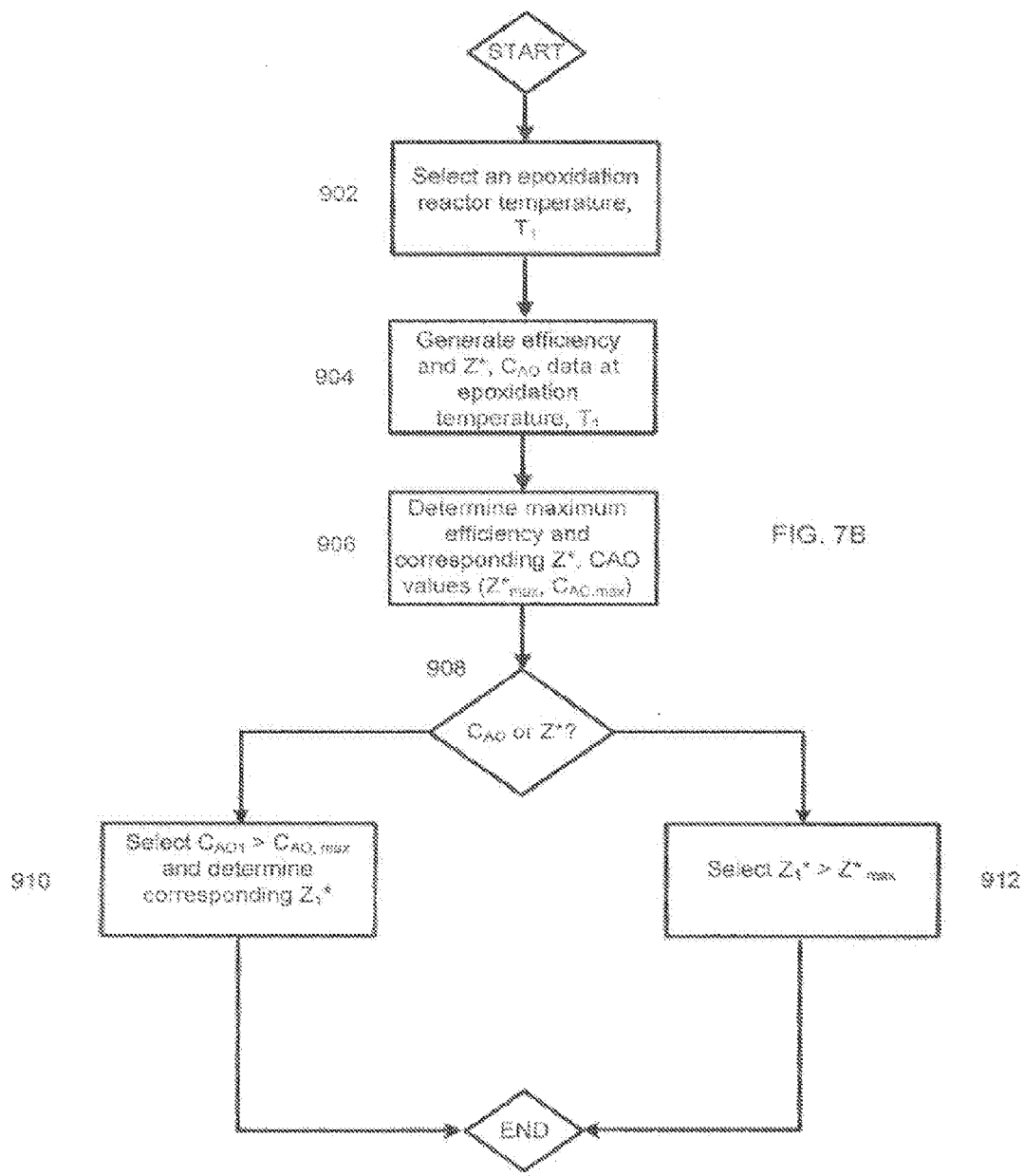
FIG. 7B is a flow chart depicting a second exemplary method of determining an optimum operating condition in the process of FIG. 1A.

Referring to FIG. 7B, a method of implementing the exemplary embodiment to select an initial optimum operating condition is depicted. As with the method of FIG. 7A, the method of FIG. 7B is not an optimization method. However, it is a method that can be used to identify an operating point that achieves a optimal efficiency. In accordance with the method, in step 902 $T_1$ is selected as described in the previous embodiment. In step 904, efficiency values are determined in the same manner as described above for step 804 in FIG. 7A. In step 906, a maximum efficiency value for $T_1$ is determined and the corresponding efficiency-maximizing $Z^*$ and $C_{AO}$ values ($Z^*_{max}$ and $C_{AO\,max}$) are determined. In one illustrative example, the maximum efficiency value is determined by plotting the collected values of efficiency versus $Z^*$ and/or $C_{AO}$ and graphically and/or numerically determining (e.g., via interpolation) the maximum efficiency, $Z^*_{max}$ and/or $C_{AO,\,max}$. In step 908, it is determined whether to select $Z_1^*$ based on the efficiency maximizing value (at constant temperature) of $Z^*$ (i.e., $Z^*_{max}$) or to first select a reactor outlet alkylene oxide concentration $C_{AO1}$ based on the efficiency maximizing value (at constant temperature) of $C_{AO}$ (i.e., $C_{AO\,max}$). If the latter method is selected, $C_{AO1}$ is selected to be greater than $C_{AOmax}$ in step 910. $C_{AO1}$ is preferably at least one percent greater than $C_{AOmax}$ (i.e., at least $1.01C_{AOmax}$), more preferably at least 5 percent greater than $C_{AOmax}$, and even more preferably at least 10 percent greater than $C_{AO\,max}$. $C_{AO1}$ is preferably no more than 25 percent greater than $C_{AO\,max}$ (i.e., no more than $1.25C_{AOmax}$), more preferably no more than 20 percent greater than $C_{AOmax}$, and even more preferably no more than 15 percent greater than $C_{AO,\,max}$. Based on the selected value of $C_{AO1}$, the necessary value of $Z_1^*$ to achieve $C_{AO1}$ and the corresponding efficiency can then be determined from the collected data.

If $C_{AO}$ is not used to determine $Z_1^*$, then in step 912 $Z_1^*$ is selected to be greater than the efficiency-maximizing value of $Z^*$ (i.e., $Z^*_{max}$). $Z_1^*$ is preferably at least one percent greater than $Z^*_{max}$ (i.e., at least $1.01Z^*_{max}$) more preferably at least 5 percent greater than $Z^*_{max}$, and more preferably at least 10 percent greater than $Z^*_{max}$. $Z_1^*$ is preferably not more than 25 percent greater than $Z^*_{max}$ (i.e., not more than $1.25Z^*_{max}$), more preferably not more than 20 percent greater than $Z^*_{max}$, and even more preferably not more than 15 percent greater than $Z^*_{max}$. The selection of $Z_1^*$, and $T_1$ will determine $C_{AO1}$ and a corresponding efficiency.

The method of FIG. 7B can also be used to identify an optimum operating point for purposes of evaluating the effect of a process parameter change made to reduce the value of an alkylene oxide production parameter. For example, referring again to the method of FIG. 3, a process parameter such as the feed gas oxygen concentration (step 306) may be reduced to reduce the value of a particular alkylene oxide production parameter. The change in the process parameter will result in a new process operating point, i.e., a new reaction temperature, feed gas oxygen concentration, and alkylene oxide concentration in the reaction product. Using the new process operating point, efficiency, $Z^*$ and $C_{AO}$ data may be generated in step 904 by varying $Z^*$ at the new reaction temperature and other process conditions. In step 906, the data thus generated are used to determine the $Z^*$ and $C_{AO}$ values ($Z^*_{max}$, $C_{AO\,max}$) at which efficiency is maximized. In step 908, either $Z^*$ or $C_{AO}$ may be used to determine an optimum efficiency at the reaction temperature. In certain embodiments, the value of $Z^*$ corresponding to the optimum efficiency is preferably at least one percent greater than $Z^*_{max}$, (i.e., at least $1.01Z^*_{max}$) more preferably at least 5 percent greater than $Z^*_{max}$, and more preferably at least 10 percent greater than $Z^*_{max}$. The value of $Z^*$ corresponding to the optimum efficiency is preferably not more than 25 percent greater than $Z^*_{max}$ (i.e., not more than $1.25Z^*_{max}$), more preferably not more than 20 percent greater than $Z^*_{max}$, and even more preferably not more than 15 percent greater than $Z^*_{max}$. As a result, the optimum efficiency may be determined and compared to the actual efficiency achieved as a result of reducing the feed gas oxygen concentration in step 306 (FIG. 3). If the actual efficiency deviates from the optimum efficiency by less than a pre-selected amount, the feed gas oxygen concentration may be further reduced to further reduce the alkylene oxide production parameter towards its target value $AO_T$. Otherwise, another process variable is preferably adjusted, such as by reducing the feed gas alkylene concentration in step 308. Thus, the method of FIG. 7B may be used to evaluate the effect of process parameter changes including those shown in FIGS. 2-6 and to constrain the extent to which any particular parameter is changed, thereby preserving optimum operation.

As shown in FIG. 1B, it has been found that the relationship between efficiency and alkylene oxide concentration when varying $Z^*$ at a constant temperature (while also holding reactor inlet alkylene concentration constant and operating at a fixed process condition) defines a curve having the shape of a downward opening parabola, and that increasing the reaction temperature shifts the parabola downward and to the right. Increasing $Z^*$ at constant temperature (while also holding the reactor inlet alkylene concentration constant and operating at a fixed process condition) moves the process along the efficiency vs. alkylene oxide curve in the direction of increasing alkylene oxide concentration. As mentioned previously, the fixed process condition is one at which at least one of reactor inlet oxygen concentration, reactor inlet carbon dioxide concentration, reactor pressure, and gas hourly space velocity is held constant. More preferably, each of these variables is held constant. It has also been found that the optimum (efficiency-maximizing) combinations of reaction temperature and overall catalyst chloriding effectiveness values over a range of alkylene oxide production rates are defined by a line (shown in FIG. 1B) that is tangent to the series of parabolic-shaped curves described above which define the relationship between efficiency and alkylene oxide concentration at various temperatures. Thus, for a given reactor inlet alkylene concentration and fixed process condition (as defined above), a selected alkylene oxide concentration corresponds to an efficiency-maximizing combination of reaction temperature and overall chloriding effectiveness. In other words, the alkylene oxide concentration corresponds to a point on the tangent line and to a temperature that corresponds to the efficiency vs. alkylene oxide concentration parabola to which the line is tangent at the selected alkylene oxide concentration. The selected alkylene oxide concentration also corresponds to a specific efficiency-maximizing value of $Z^*$ at the specified concentration. Referring again to FIG. 1B, the indicated tangent line intersects the 245° C. (upper left) parabola at 1.4 mole percent ethylene oxide and 89.8% efficiency. Thus, for a 1.4 mole percent ethylene oxide concentration, the optimum efficiency will be 89.8%, the optimum temperature will be 245° C., and the optimum $Z^*$ will be slightly greater than 4.7.

The optimum temperature and overall chloriding effectiveness values may be determined, if necessary, by interpolation or extrapolation from plots of alkylene oxide concentration versus temperature and overall chloriding effectiveness values corresponding to the points used to construct the tangent line. The overall chloriding effectiveness values used to construct the tangent line may also themselves be interpolated or extrapolated from actual experimental data in order to define the temperature and overall chloriding effectiveness value $Z^*$ combination at the point of tangency for the relevant efficiency versus alkylene oxide concentration curve.

The slope of the tangent line intersecting the efficiency versus alkylene oxide concentration curves generated for a specific high efficiency silver catalyst at a plurality of temperatures is frequently no greater than −1 percent efficiency/mole percent alkylene oxide, more frequently no greater than −1.5 percent efficiency/mole percent alkylene oxide, and even more frequently no greater than −2 percent efficiency/mole percent alkylene oxide. The slope is frequently at least −5 percent efficiency/mole percent alkylene oxide, more frequently at least −4.5 percent efficiency/mole percent alkylene oxide, and even more frequently at least −4 percent efficiency/mole percent alkylene oxide. A slope of −3 percent efficiency/mole percent alkylene oxide is most frequent. Put differently, in certain examples, in steps 202, 302, 402, 502, and/or 602, the initial reaction temperature and overall chloriding effectiveness values $T_1$ and $Z_1^*$ lie on a tangent line having a slope that falls within the foregoing ranges when varying $Z^*$ at constant temperature, constant reactor inlet alkylene concentration and at a fixed process condition. The fixed process condition is one at which at least one variable selected from the group consisting of reactor inlet oxygen and carbon dioxide concentration, reactor pressure, and gas hourly space velocity is held constant, and more preferably is a condition at which each of these variables is held constant.

The foregoing method may also be used to identify an optimum operating point at the process condition established by a process parameter change that is made to reduce the value of an alkylene oxide production parameter. Again using FIG. 3 as an example, in step 306 the feed gas concentration of oxygen is reduced to reduce the value of the alkylene oxide production parameter, yielding a new operating point comprising a new feed gas oxygen concentration, a new reaction temperature, and a new alkylene oxide reaction product concentration. Using the conditions comprising the new operating point (except for T and $Z^*$), a tangent line may be constructed as described above. The new alkylene oxide production parameter (e.g., $C_{AO}$) will correspond to an optimum efficiency defined by the tangent line. The actual efficiency at the new operating point may be compared to the efficiency defined by the tangent line to determine the deviation from optimum operation. If the actual efficiency deviates from the optimum efficiency by more than a desired value, another process parameter (e.g., feed gas alkylene concentration in step 306) is used to effect any further changes in the alkylene oxide production parameter that are desired.

As discussed above, in one preferred embodiment, the initial reaction temperature $T_1$ and initial overall catalyst chloriding effectiveness $Z_1^*$ are selected by an optimization process that involves maximizing the efficiency of process 20 to alkylene oxide concentration at the desired alkylene oxide production parameter (e.g., reactor outlet alkylene oxide concentration). The same technique may be used to define an optimum operating condition at a new operating point established by manipulating a process parameter to achieve a desired reduction in an alkylene oxide production parameter.

Figure 7C:
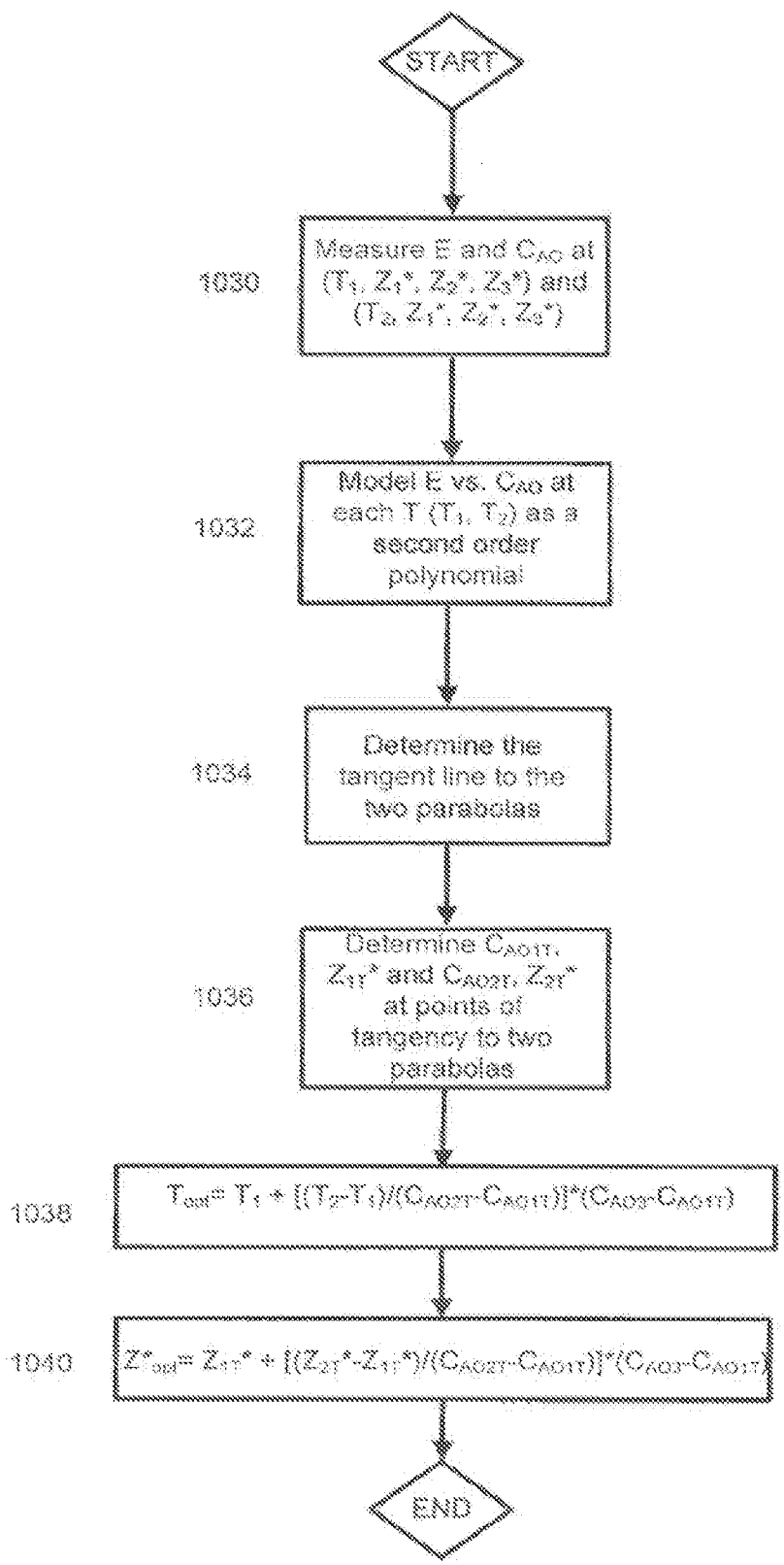
FIG. 7C is a flow chart depicting a third exemplary method of determining an optimum operating condition in the process of FIG. 1A.

An exemplary method of performing the optimization is provided in FIG. 7C. In accordance with the method, efficiency data (E) and reactor outlet alkylene oxide concentration data ($C_{AO}$) are collected at two temperatures ($T_1$ and $T_2$) and at least three overall catalyst chloriding effectiveness values ($Z_1^*$, $Z_2^*$, $Z_3^*$) for each of the temperatures (step 1030), which may be the same or different for each of the two temperatures. The reactor inlet alkylene concentration is preferably held constant and a fixed process condition is preferably employed as the temperature and $Z^*$ are varied. The fixed process condition is as described previously. The relationship between E and $C_{AO}$ at each temperature as $Z^*$ is varied among the three values $Z_1^*$, $Z_2^*$, and $Z_3^*$ is modeled as a second order polynomial, thereby yielding two parabolas with the parabola for the higher temperature ($T_2$) being shifted downward and to the left from the parabola for the lower temperature ($T_1$) on a plot of E vs. $C_{AO}$ (step 1032). The line that is tangent to both parabolas (e.g., $E = m(C_{AO}) + b$, where m is the slope and b is the y-intercept) is then determined (step 1034), and the two reactor outlet alkylene oxide concentrations ($C_{AO1T}$ and $C_{AO2T}$) at the points of tangency for each parabola are determined (step 1036), as are the corresponding values of $Z^*$ at the points of tangency ($Z_{1T}^*$ and $Z_{2T}^*$) (step 1036). It may be necessary to interpolate between the values of $Z_1^*$, $Z_2^*$, and $Z_3^*$ from step 1030 to obtain $Z_{1T}^*$ and $Z_{2T}^*$. For an initial selected reactor outlet concentration of alkylene oxide, $C_{AO3}$, the optimal values of the reaction temperature and overall chloriding effectiveness can be calculated as follows:

$$T_{opt}=T_1+[(T_2-T_1)/(C_{AO2T}-C_{AO1T})]*(C_{AO3}-C_{AO1T}) \quad \text{(step 1038)} \tag{6}$$

$$Z^*_{opt}=Z_{1T}^*+[(Z_{2T}^*-Z_{1T}^*)/(C_{AO2T}-C_{AO1T})]*(C_{AO3}-C_{AO1T})(\text{step }1040) \tag{7}$$

$T_{opt}$ and $Z^*_{opt}$ can then be used as $T_1$ and $Z_1^*$ in step 1012 of the method of FIG. 3.

In certain exemplary implementations of the methods of FIGS. 2-6, the efficiency to the alkylene oxide is stable following the adjustment of the at least one process parameter comprising feed gas oxygen concentration. In accordance with such exemplary implementations, the efficiency preferably varies by no more than 0.8 percent per day, more preferably by no more than 0.5 percent per day, and still more preferably by no more than 0.3 percent per day following the adjustment of feed gas oxygen concentration, feed gas alkylene concentration, reactor feed gas inlet pressure, and/or feed gas carbon dioxide concentration.

Example 1

A single pass continuous stirred tank reactor (CSTR) is loaded with 50 ml of whole pills of a high efficiency ethylene oxide catalyst. The catalyst is operated for 41 days and is lined out at an initial reactor outlet ethylene oxide concentration of 2.0%. The initial reaction temperature prior to the rate reduction is controlled to 240° C. to maintain the target ethylene oxide production rate. The initial reactor inlet pressure is 2000 kPa, and the initial gas hourly space velocity is 6900 h$^{-1}$. The initial reactor feed gas molar composition is 30.0% ethylene, 8.0% oxygen, 1.0% carbon dioxide, 0.6% ethane, and the balance is nitrogen. The feed gas also includes an ethyl chloride gas phase promoter with a molar concentration that is controlled to maintain an optimum Z* value of 3.5.

On day 41, the target reactor outlet ethylene oxide molar concentration is reduced from 2.0% to 1.2%. To achieve the reduction in ethylene oxide molar concentration, the molar concentration of oxygen in the feed gas is reduced from 8.0% to 4.0%, the molar concentration of ethylene in the feed gas is reduced from 30.0% to 25.0%, and the pressure is reduced from 2000 kPa to 1890 kPa. To simulate the effects of using a constant speed recycle gas compressor, the gas hourly space velocity is reduced in proportion to the reduction of the reactor pressure, i.e., from 6900 h$^{-1}$ to 6300 h$^{-1}$. The concentration of ethyl chloride in the reactor feed gas is reduced from 3.15 ppm to 2.98 ppm to maintain Z* at 3.5. The foregoing changes are made almost simultaneously.

Figure 8A:
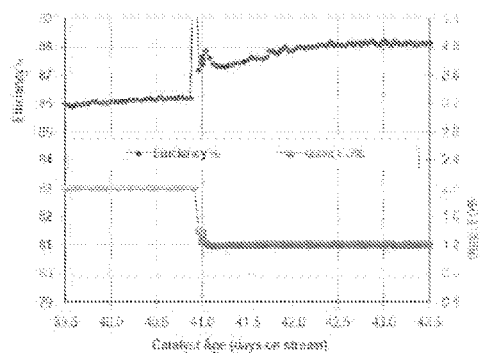
FIG. 8A is a graph depicting efficiency and reactor product ethylene oxide concentration data used to illustrate an exemplary a method of reducing ethylene oxide concentration by reducing feed gas oxygen concentration, feed gas alkylene concentration, and reactor inlet pressure in a process for producing ethylene oxide using a high-efficiency catalyst.
Figure 8B:
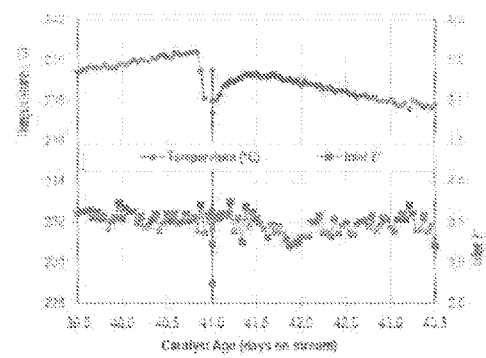
FIG. 8B is a graph depicting reaction temperature and overall chloriding effectiveness data used to illustrate the exemplary method of FIG. 8A.

The results of the foregoing process changes are depicted in FIGS. 8A-8B. As the figures indicate, the efficiency increases from about 86% to about 88% whereas the reaction temperature decreases by about 2° C. Thus, the method of Example 1 effectively decreases the concentration of ethylene oxide in the reaction product without requiring the manipulation of reaction temperature and/or overall chloriding effectiveness.

Example 2 (Comparative)

The comparative example is carried out using the same process as in Example 1 following the process changes that are described therein. On day 44, the catalyst is briefly shut down. Following re-start at the same conditions used prior to shut-down, steady-state operation is re-established after 3 days. The same 88% efficiency is obtained, but the reaction temperature is 2° C. higher than before. On day 48, the reactor outlet ethylene oxide concentration is 1.2%, but the process conditions are reversed relative to the changes made in Example 1 to restore the initial concentrations of feed gas oxygen and ethylene, the initial reactor pressure, and the initial gas hourly space velocity used therein.

Figure 9A:
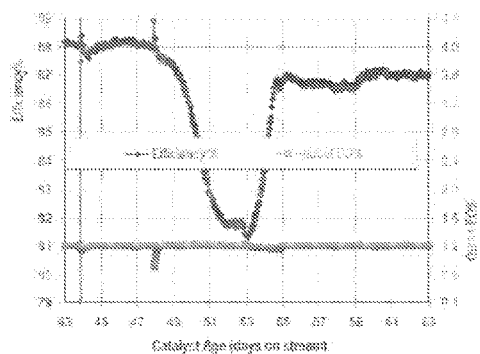
FIG. 9A is a graph depicting efficiency and reactor product ethylene oxide concentration data used to illustrate a conventional method of reducing ethylene oxide concentration by reducing reaction temperature in a process for producing ethylene oxide using a high-efficiency catalyst.
Figure 9B:
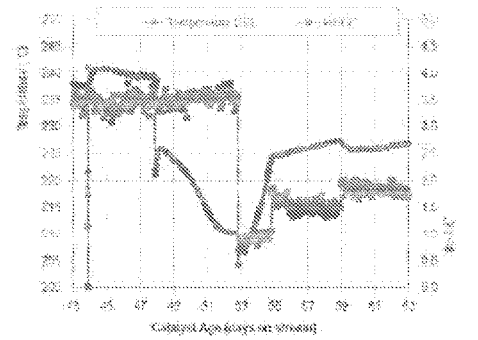
FIG. 9B is a graph depicting reaction temperature and overall chloriding effectiveness used to illustrate the conventional method of FIG. 9A.

To demonstrate the effects of using conventional techniques for reducing the reactor outlet ethylene oxide concentration, the reaction temperature is manually reduced to 225° C. based on a kinetic estimation of the temperature required to achieve an ethylene oxide concentration of 1.2%. The reactor is then placed on automatic temperature control to maintain the selected ethylene oxide concentration. The ethyl chloride and Z* values are not optimized prior to making these changes but are later adjusted (around day 53) to maximize efficiency. As shown in FIGS. 9A and 9B, the reaction temperature and efficiency experience strong variations that are difficult to manage. In addition, the process takes a relatively longer time (compared to Example 1) to re-optimize, and even after optimization, the process efficiency is about 1% lower than in Example 1.

Example 3

Figure 10A:
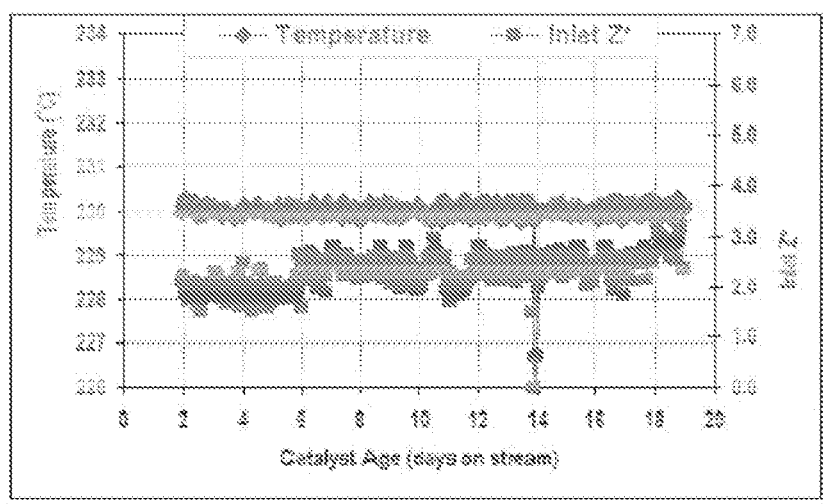
FIG. 10A is a graph depicting reaction temperature and overall chloriding effectiveness used to illustrate an exemplary method of reducing ethylene oxide concentration by reducing feed gas oxygen concentration in a process for producing ethylene oxide using a high-efficiency catalyst.

A feed gas comprising 35.0 mole % ethylene, 0.6% mole ethane, 8.0 mole % oxygen, 2.0 mole % CO2 and 1.9-2.1 ppmv ethyl chloride, and the balance nitrogen is introduced to a high efficiency, rhenium-promoted silver catalyst loaded in a pilot plant reactor with reactor volume of 3.55 liters. The reactor pressure is 2135 kPa, and the total feed gas flow rate is 19169 standard liters per hr. The inlet coolant temperature is 230° C. throughout the run. Inlet coolant temperature (upper trend) and Z* (lower trend) profiles are given in FIG. 10A.

Figure 10B:
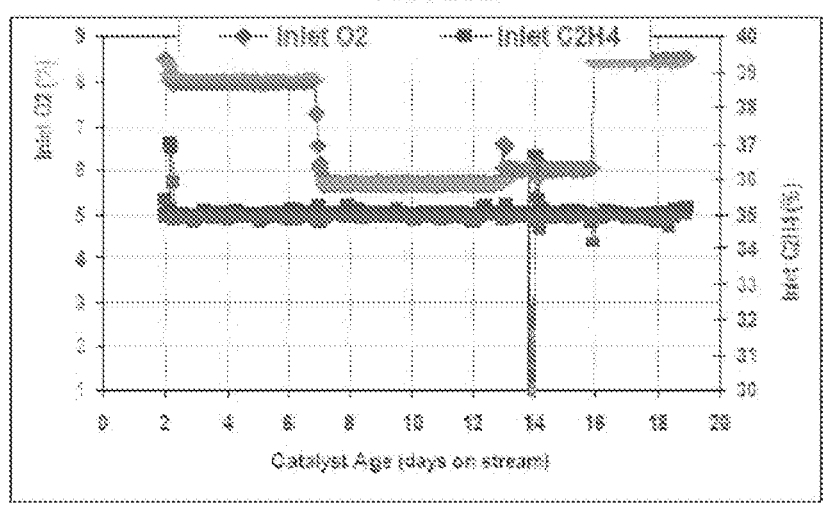
FIG. 10B is a graph depicting feed gas oxygen concentration and feed gas ethylene concentration used to illustrate the exemplary method of FIG. 10A.

As shown in FIG. 10C, by day 6.5, the delta ethylene oxide molar concentration (lower trend) is increased to 2.66%, and catalyst efficiency (upper trend) has attained a stable value of 85.7%. On day 7, the molar concentration of oxygen in the feed gas is reduced from 8.0% to 5.7% without changing any other process variables. The trends for oxygen (upper trend) and ethylene molar concentration (lower trend) are given in FIG. 10B. On day 7, the delta ethylene oxide molar concentration is reduced to 2.2% as a result of the drop in oxygen molar concentration in the feed gas composition. During the same time, the catalyst selectivity increases to an average value of 86.0% from 85.7%. The reduction in oxygen molar concentration results in a decrease in the delta ethylene oxide molar concentration without requiring the manipulation of other process variables to maintain optimum efficiency. From day 16 onward, the molar concentration of oxygen in the feed gas is increased to 8.5%. By day 18, the delta ethylene oxide molar concentration increases to 2.6%, and catalyst efficiency reaches 86.0%. Thus, this example illustrates the use of feed gas oxygen concentration to effect a desired change in alkylene oxide concentration without compromising efficiency.

Example 4

Figure 11A:
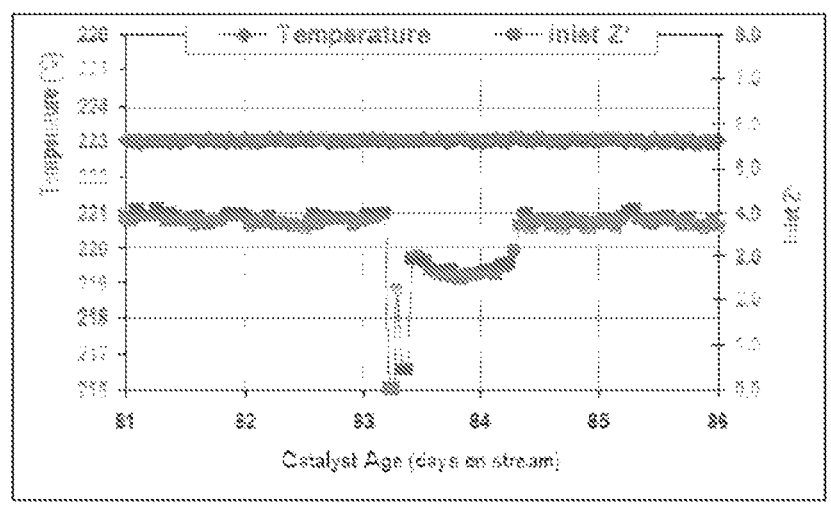
FIG. 11A is a graph depicting reaction temperature and overall catalyst chloriding effectiveness used to illustrate the effects of decreasing oxygen concentration on reactor product ethylene oxide concentration when operating at a non-optimal and optimal overall catalyst chloriding effectiveness.

A feed gas comprising 35.0 mole % ethylene, 0.6 mole % ethane, 8.5 mole % oxygen, 1.0 mole % CO2 and 3.2 ppmv ethyl chloride, and the balance nitrogen is introduced to a high efficiency, rhenium-promoted silver catalyst loaded in a pilot plant reactor with reactor volume of 3.20 liters. The reactor pressure is 2135 kPa, and the total feed gas flow rate is 17245 standard liters per hr. The inlet coolant temperature is 223° C. throughout the run. Inlet coolant temperature (upper trend) and Z* (lower trend) profiles are given in FIG. 11A.

Figure 11B:
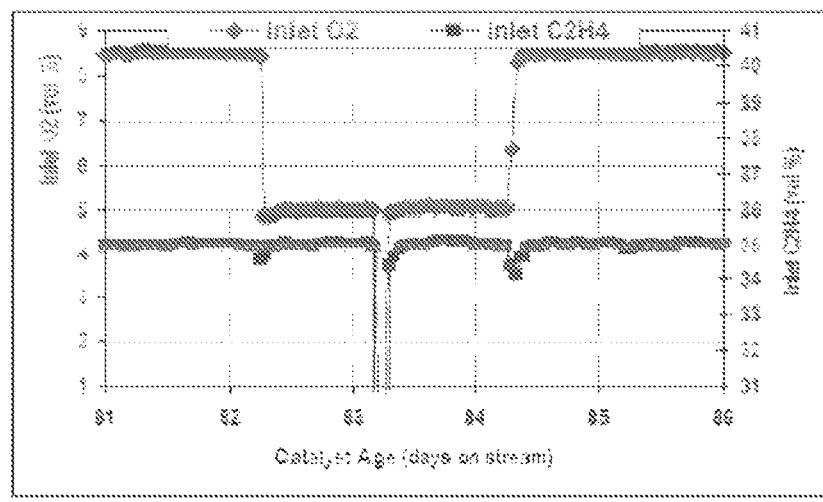
FIG. 11B is a graph depicting feed gas oxygen and feed gas ethylene concentration used to illustrate the exemplary method of FIG. 11A.
Figure 11C:
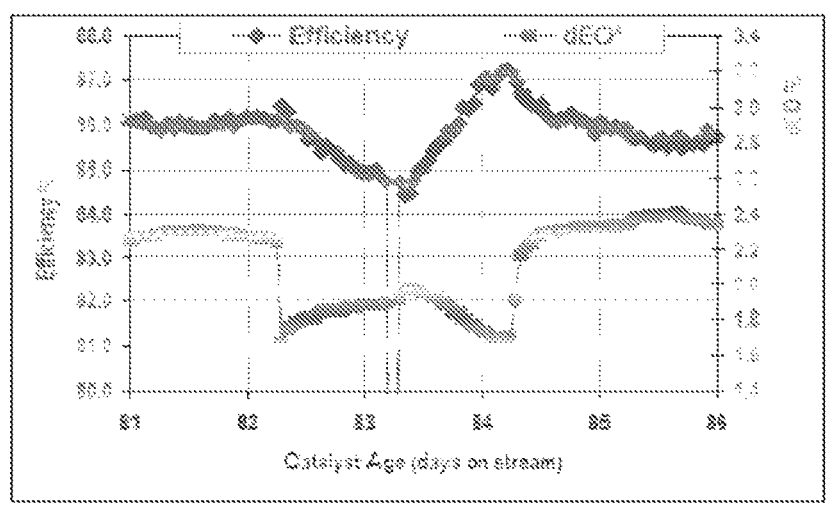
FIG. 11C is a graph depicting efficiency and reactor product delta ethylene oxide concentration data used to illustrate the exemplary method of FIG. 11A.

As shown in FIG. 11C, between days 82 to 82.5, the target delta ethylene oxide molar concentration (lower trend) decreases from 2.3% to 1.7%, and by day 83, the target delta ethylene oxide molar concentration increases to 1.9%. The catalyst efficiency (upper trend) during this time period decreases by 1.0%. To realize the reduction in ethylene oxide molar concentration, the molar concentration of oxygen in the feed gas is reduced from 8.5% to 5.0% without changing any other process variables. The trends for oxygen (upper trend) and ethylene (lower trend) molar concentration are given in FIG. 11B. The changes in delta ethylene oxide molar concentration and catalyst efficiency at lower oxygen molar concentration suggest that the chloride effectiveness factor is on the higher side of its optimum value. Thus, the catalyst is showing over-chloriding behavior.

Between days 83 to 83.5, the reaction is shut down for 2 hours, and started-up again at pre-shutdown conditions except the ethyl chloride is set at 2.1 ppmv, resulting in an average Z* value of 2.7, which is lower compared to pre-trip conditions. As shown in FIG. 11C, after restart, by day 84, the target delta ethylene oxide molar concentration is reached at 1.7% and catalyst efficiency increases to 87.2%. Between days 84 to 85, the molar concentration of oxygen in the feed gas is again increased back to 8.5%. By day 86, the delta ethylene oxide molar concentration increases to 2.3%, and catalyst efficiency reaches 86.0%. Thus, when Z* is initially at an optimum value, feed gas oxygen can be adjusted to attain a desired delta ethylene oxide concentration without requiring the adjustment of other process variables to maintain an optimum efficiency.

What is claimed is:

1. A method for reducing the value of an alkylene oxide production parameter in a process for making the alkylene oxide by reacting a feed gas comprising an alkylene, oxygen, and at least one organic chloride over a high-efficiency silver catalyst, the method comprising the steps of:
   operating the process at a first reaction temperature, a first overall catalyst chloriding effectiveness value, and a first concentration of oxygen in the feed gas to yield a first value of the alkylene oxide production parameter;
   selecting a target value of the alkylene oxide production parameter, wherein the target value of the alkylene oxide production parameter is less than the first value of the alkylene oxide production parameter; and
   adjusting at least one process parameter such that the alkylene oxide production parameter decreases, wherein the step of adjusting at least one process parameter comprises first decreasing the concentration of oxygen in the feed gas.

2. The method of claim 1, wherein the step of adjusting at least one process parameter comprises second adjusting the concentration of the alkylene in the feed gas.

3. The method of claim 1, wherein the step of adjusting at least one process parameter comprises second adjusting the feed gas pressure.

4. The method of claim 1, wherein the step of adjusting at least one process parameter comprises second adjusting the concentration of carbon dioxide in the feed gas.

5. The method of claim 1, wherein the overall catalyst chloriding effectiveness value of the process is held constant during the step of adjusting at least one process parameter.

6. The method of claim 1, wherein during the step of adjusting at least one process parameter, the reaction temperature varies by no more than 5° C.

7. The method of claim 1, wherein the process has an optimum efficiency that varies with both the reaction temperature and the concentration of the alkylene oxide in the reaction product under a constant pressure, and the step of adjusting at least one process parameter yields an efficiency to the alkylene oxide that varies from the optimum efficiency by no more than 0.5%.

8. The method of claim 1, wherein the first overall catalyst chloriding effectiveness value and the first reaction temperature are selected to provide the maximum efficiency toward the alkylene oxide at the first value of the alkylene oxide production parameter.

9. The method of claim 1, wherein the concentration of the alkylene in the feed gas is no less than 20 mole percent.

10. The method of claim 1, wherein the concentration of oxygen in the feed gas is no greater than 95% of the oxygen flammability concentration.

11. The method of claim 1, wherein the concentration of oxygen in the feed gas is no less than 1.0 mole percent.

12. A process for reducing the value of an alkylene oxide production parameter, comprising the steps of:
   reacting a feed gas comprising an alkylene, oxygen, and an at least one organic chloride over a high efficiency silver catalyst to yield a reaction product having a first value of the alkylene oxide production parameter, wherein the feed gas has a first overall catalyst chloriding effectiveness value and a first oxygen concentration, and the reaction is carried out at a first reaction temperature and a first feed gas pressure;
   selecting a target value of the alkylene oxide production parameter;
   decreasing the concentration of oxygen in the feed gas to a second oxygen concentration while maintaining the overall chloriding effectiveness at the first overall catalyst chloriding effectiveness value until the alkylene oxide production parameter is no greater than the target value or the reaction temperature decreases by a preselected maximum amount.

13. The process of claim 12, wherein the second oxygen concentration is no less than 1.0 mole percent.

14. The process of claim 12, wherein the first oxygen concentration is no greater than 95% of the oxygen flammability concentration.

15. The process of claim 12, wherein the pre-selected maximum reaction temperature decrease is no more than 5° C.

* * * * *